US011942188B2

(12) United States Patent
Shi et al.

(10) Patent No.: US 11,942,188 B2
(45) Date of Patent: Mar. 26, 2024

(54) OBTAINING AN IMPROVED THERAPEUTIC LIGAND

(71) Applicant: UCB Biopharma SRL, Brussels (BE)

(72) Inventors: Jiye Shi, Brussels (BE); Terence Seward Baker, Slough (GB); Alastair David Griffiths Lawson, Slough (GB); Xiaofeng Liu, Slough (GB)

(73) Assignee: UCB Biopharma SRL, Brussels (BE)

( * ) Notice: Subject to any disclaimer, the term of this patent is extended or adjusted under 35 U.S.C. 154(b) by 654 days.

(21) Appl. No.: 16/823,055

(22) Filed: Mar. 18, 2020

(65) Prior Publication Data

US 2021/0005277 A1 Jan. 7, 2021

Related U.S. Application Data

(63) Continuation of application No. 14/897,459, filed as application No. PCT/EP2014/062478 on Jun. 13, 2014, now abandoned.

(30) Foreign Application Priority Data

Jun. 13, 2013 (GB) ..................................... 1310544

(51) Int. Cl.

*G16C 20/50* (2019.01)
*C07K 16/24* (2006.01)
*G16B 5/00* (2019.01)
*G16B 15/00* (2019.01)
*G16B 15/30* (2019.01)
*G16C 20/90* (2019.01)

(52) U.S. Cl.

CPC .............. *G16B 5/00* (2019.02); *C07K 16/244* (2013.01); *G16B 15/30* (2019.02); *G16C 20/50* (2019.02); *G16C 20/90* (2019.02); *C07K 2317/55* (2013.01); *C07K 2317/76* (2013.01); *G16B 15/00* (2019.02)

(58) Field of Classification Search

CPC ......... G16B 15/00; G16B 15/30; G16C 20/50
See application file for complete search history.

(56) References Cited

U.S. PATENT DOCUMENTS

| | | | |
|---|---|---|---|
| 5,331,573 | A | 7/1994 | Balaji et al. |
| 8,303,953 | B2 | 11/2012 | Adams et al. |
| 2004/0229290 | A1 | 11/2004 | Hellinga et al. |
| 2006/0100789 | A1 | 5/2006 | Itai et al. |
| 2007/0061118 | A1 | 3/2007 | Friesner et al. |

FOREIGN PATENT DOCUMENTS

| | | |
|---|---|---|
| EP | 2216429 | 8/2010 |
| JP | 2005181104 | 7/2005 |
| WO | WO 01/97098 | 12/2001 |
| WO | WO 02/16930 | 2/2002 |
| WO | 2008/047134 | 4/2008 |
| WO | WO 2008/144776 | 11/2008 |
| WO | WO 2009/064015 | 5/2009 |
| WO | 2009/130459 | 10/2009 |
| WO | WO 2012/005800 | 1/2012 |
| WO | 2012/095662 | 7/2012 |

OTHER PUBLICATIONS

Virshup, A.M., Contreras-García, J., Wipf, P., Yang, W. and Beratan, D.N. Stochastic voyages into uncharted chemical space produce a representative library of all possible drug-like compounds. Journal of the American Chemical Society, 135(19), pp. 7296-7303. (Year: 2013).*
McConnell, A.D., et al.. An integrated approach to extreme thermostabilization and affinity maturation of an antibody. Protein Engineering, Design & Selection, 26(2), p. 1151-164. (Year: 2013).*
Tiller, K.E. and Tessier, P.M. Advances in antibody design. Annual Review of Biomedical Engineering, 17, pp. 191-216. (Year: 2015).*
Kitova, E.N., El-Hawiet, A., Schnier, P.D. and Klassen, J.S., 2012. Reliable determinations of protein-ligand interactions by direct ESI-MS measurements. Are we there yet?. Journal of the American Society for Mass Spectrometry, 23(3), pp. 431-441. (Year: 2012).*
Gloster, T.M. Development of inhibitors as research tools for carbohydrate-processing enzymes. Biochemical Society Transactions, 40(5), pp. 913-928. (Year: 2012).*
Flores, J., White, B.M., Brea, R.J., Baskin, J.M. and Devaraj, N.K. Lipids: chemical tools for their synthesis, modification, and analysis. Chemical Society Reviews, 49(14), pp. 4602-4614. (Year: 2020).*
Laskowski, R.A., Thornton, J.M., Humblet, C. and Singh, J. X-SITE: use of empirically derived atomic packing preferences to identify favourable interaction regions in the binding sites of proteins. Journal of molecular biology, 259(1), pp. 175-201. (Year: 1996).*
Laskowski et al., "X-SITE: use of empirically derived atomic packing preferences to identify favourable interaction regions in the binding sites of proteins," (1996) Journal of Molecular Biology, 259, pp. 175-201.
Fujino et al., "Robust in vitro affinity maturation strategy based on interface-focused high-throughput mutational scanning," Biochem. Biophys. Res. Comm., 428, pp. 395-400.
Kuroda et al., "Computer-aided antibody design," Prot. Eng. Design & Selection, 25, pp. 507-521.

(Continued)

*Primary Examiner* — Lori A. Clow
*Assistant Examiner* — Janna Nicole Schultzhaus
(74) *Attorney, Agent, or Firm* — McDonnell Boehnen Hulbert & Berghoff LLP

(57) ABSTRACT

Methods and associated apparatus involving designing a ligand ab initio that will bind to a binding site of a macromolecular target, or of identifying a modification to a ligand for improving the affinity of the ligand to a binding site of a macromolecular target, comprising using information about non-bonding, intra-molecular or inter-molecular atom to atom contacts extracted from a database of biological macromolecules to identify favoured regions adjacent to the binding site for particular atom types and modifying a candidate ligand to increase the intersection between atoms of the candidate ligand and the favoured regions. One or more steps of the methods may be performed by a computer.

19 Claims, 12 Drawing Sheets

(56) References Cited

OTHER PUBLICATIONS

Lippow et al., "Computational design o antibody-affinity improvement byond in vio maturation," Nat Biotech. (2007) 25, pp. 1171-1176.
Barderas et al., "Affinity maturation of antibodies assisted by in silico modelling," (2008) PNAS, 105, pp. 9029-9034.
Rohs et al., "Molecular flexibility in ab initio drug docking to DNA: binding-site and binding-mode transitions in all-atom Monte Carlo simulations," Nucleic Acids Research, 2005, vol. 33, No. 22, pp. 7048-7057.
Nisius et al., "Structure-based computational analysis of protein binding sites for function and druggability prediction," Journal of Biotechnology 159 (2012) pp. 123-134.
Neuvirth et al., "ProMate: A Structure Based Prediction Program to Identify the Location of Protein-Protein Binding Sites," J. Mol. Biol. (2004) 338, pp. 181-199.
Kaminski et al, "Evaluation and Reparametrization of the OPLS-AA Force Field for Proteins via Comparison with Accurate Quantum Chemical Calculations on Peptides," J. Phys. Chem. B 2001, 105, 6474-6487.
Jorgensen et al, "Development and Testing of the OPLS All-Atom Force Field on Conformational Energetics and Properties of Organic Liquids," J. Am. Chem. Soc., 1996, 118(45), 11225-11236.
Morrow et al, "Computational Prediction of Protein Hot Spot Residues," Current Pharmaceutical Design, 2012, 18, 1255-1265.
Written Opinion dated Apr. 25, 2017 from the Intellectual Property Office of Singapore for Application No. 11201510084T filed Jun. 13, 2014, 11 pages.
Japanese office action dated Apr. 4, 2018 for Japanese Application No. 2016-518523.
Office Action and Search Report dated Mar. 22, 2018 issued for the corresponding Russian application No. 2016100234, 13 pages.

* cited by examiner

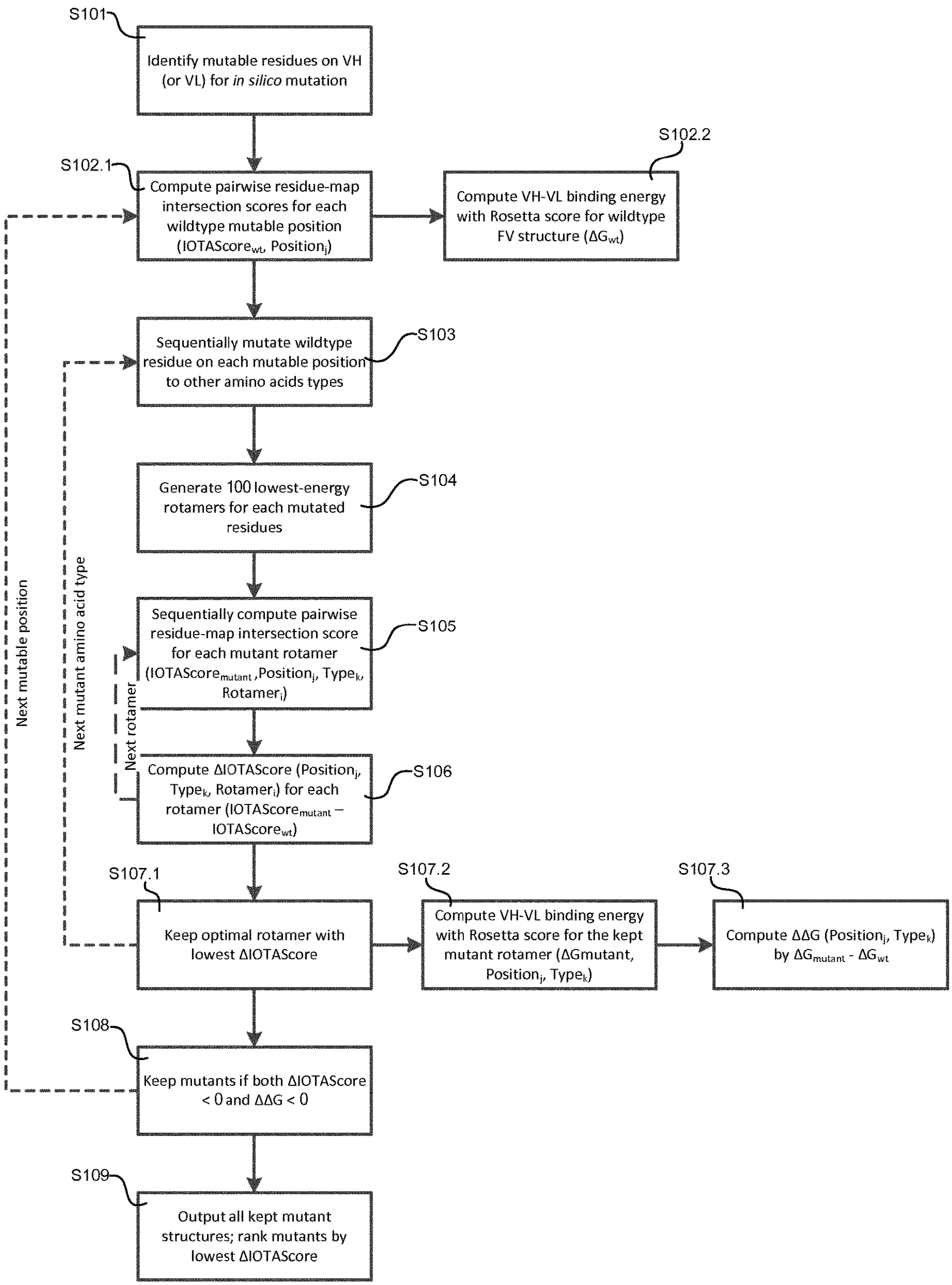

Fig. 14

```
S101 → Identify mutable residues on VH (or VL) for in silico mutation
  ↓
S102.1 → Compute pairwise residue-map intersection scores for each wildtype mutable position (IOTAScore_wt, Position_j)
  → S102.2: Compute VH-VL binding energy with Rosetta score for wildtype FV structure (ΔG_wt)
  ↓
S103 → Sequentially mutate wildtype residue on each mutable position to other amino acids types
  ↓
S104 → Generate 100 lowest-energy rotamers for each mutated residues
  ↓
S105 → Sequentially compute pairwise residue-map intersection score for each mutant rotamer (IOTAScore_mutant, Position_j, Type_k, Rotamer_i)
  ↓
S106 → Compute ΔIOTAScore (Position_j, Type_k, Rotamer_i) for each rotamer (IOTAScore_mutant − IOTAScore_wt)
  ↓
S107.1 → Keep optimal rotamer with lowest ΔIOTAScore
  → S107.2: Compute VH-VL binding energy with Rosetta score for the kept mutant rotamer (ΔGmutant, Position_j, Type_k)
  → S107.3: Compute ΔΔG (Position_j, Type_k) by ΔG_mutant − ΔG_wt
  ↓
S108 → Keep mutants if both ΔIOTAScore < 0 and ΔΔG < 0
  ↓
S109 → Output all kept mutant structures; rank mutants by lowest ΔIOTAScore
```

Loop labels: Next mutable position, Next mutant amino acid type, Next rotamer

OBTAINING AN IMPROVED THERAPEUTIC LIGAND

CROSS-REFERENCE TO RELATED APPLICATIONS

This application is a continuation of U.S. application Ser. No. 14/897,459, filed Dec. 10, 2015, now abandoned, which is a U.S. national phase of International Application No. PCT/EP2014/062478, filed Jun. 13, 2014, which claims priority from Great Britain Application No. GB 1310544.0, filed Jun. 13, 2013, the disclosure of each of which is hereby incorporated by reference in its entirety.

The present invention relates to obtaining an improved therapeutic ligand, in particular by determining how an existing or candidate ligand can be modified to improve binding of the ligand at a binding site on a target protein or by aiding the de novo design of a candidate ligand as a precursor to a therapeutic.

Therapeutic molecules (ligands) fall into two distinct classes: chemical entities (or novel chemical entities, NCEs) and biologicals. The former are low molecular weight organic compounds, typically of molecular weight of 500 Daltons or less, that have been chemically synthesized or isolated from natural products. These are typically derived from starting chemicals or 'hits' that are discovered by screening chemical or natural product libraries. Such hits typically have sub-optimal binding affinity for the target and considerable trial and error in chemical modification is required in order to obtain better affinity for the target (typically of affinity constant ($K_D$) low micromolar or less). It is preferable that the hit has a lower molecular weight, say 300 Daltons or less, so that subsequent chemical modification does not exceed the 500 Dalton limit. These hits are often referred to as 'fragments'. Optimisation of the hit to obtain a candidate therapeutic or lead molecule is greatly enhanced by structural information; for instance by obtaining an x-ray crystallographic structure of the protein in co-complex with the hit molecule or fragment. Such data provides insight into where on the target protein the small molecule binds and importantly indicates how atomic interactions between the two account for binding. Furthermore the topographical nature of the protein surface immediately surrounding the bound hit is revealed; and particularly if it is a cleft or a pocket, the structure will suggest how the hit might be elaborated to better fill the space within the pocket and how to make further interactions with the protein and hence improve binding affinity and specificity.

There are a number of computer based algorithms available to assist the medicinal chemist in making rational choices for chemical elaboration of the hit. These are either physics based methods that attempt to calculate the free energy of binding between the small molecule and protein from first principles (e.g. Schrodinger™ suite of software) or are statistical potential methods that rely on a database of atomic interactions extracted from collections of protein—small molecule structures (e.g. SuperStar).

Biologicals are large peptide or protein molecules (of molecular weight greater than 1000 Daltons). They are often antibodies or antibody like molecules that recognize and bind to a target molecule, usually with better affinity and specificity compared to NCEs ($K_D$ low nanomolar or less). They may also be other types of protein molecules such as hormones, cytokines, growth factors or soluble receptors.

The binding of a candidate biological therapeutic molecule to a binding site can be modified by mutating the candidate therapeutic molecule. This may be required to improve the binding affinity or alter the binding specificity. However, it is relatively time-consuming to perform the mutation and to test the binding efficiency of the mutated molecule. Many different mutations may be required before improvements in binding efficiency are obtained.

It is known to use computers to predict what kind of modifications might be most effective. However, a given molecule can be modified in a vast number of ways and it is difficult to configure a computer so that the prediction can be achieved reliably in a practical period of time.

Laskowski R A, Thornton J M, Humblet C & Singh J (1996) "X-SITE: use of empirically derived atomic packing preferences to identify favourable interaction regions in the binding sites of proteins", Journal of Molecular Biology, 259, 175-201 discloses a computer-based method for identifying favourable interaction regions for different atom types at the surface of a protein, such as at a dimer interface or at a molecular-recognition or binding site. The Laskowski et al predictions are based on a database of empirical data about non-bonding intra-molecular contacts observed in high-resolution protein structures.

In the approach of Laskowski et al, the 20 amino acids are broken up to yield a total of 488 possible 3-atom fragments. Taking chemical similarities into account these are reduced to a set of 163 fragment types that sub-divide the database. Each fragment contains a first atom (referred to as "position 3") with two further atoms defining triangulation (or spatial normalization) positions. A density function is derived by recording the various positions at which an atom (which may be referred to as a "second atom") is found to be in a non-bonding intra-molecular contact with the first atom of a 3-atom fragment.

A predicted favourable interaction region for a given atom type is obtained in Laskowski et al by transplanting density functions into the binding site. Each density function is transplanted such that the coordinates of the three atoms of the 3-atom fragment corresponding to the density function are superimposed on the coordinates of a corresponding 3-atom fragment in the binding site. Where density functions from different 3-atom fragments in the binding site overlap, an average "density" is used to predict the favourable interaction region.

The approach of Laskowski et al is relatively complex and discards potentially useful data. The density functions of Laskowski et al are obtained by populating a 3-D grid with the positions of second atom contacts for each fragment type. A different grid is used for each of the 163 fragment types. Data for each second atom type is then mathematically transformed to give the density function. Using the fragment definitions of Laskowski et al, fragment type can be shared by different atoms on the same residue and by atoms on different residues. When the Laskowski et al database has been built on these fragment types there is an over-abundance of main chain fragments that requires a down-weighting at the stage of transplanting the density functions into the binding site. Furthermore, a given fragment type can include several actual fragments with subtle differences in bond lengths and angles and concomitant differences in second atom distributions which become masked when combined in these divisions.

Short range secondary structure in the proteins used for deriving the empirical data in Laskowski et al can lead to bias and reduces the efficiency with which the empirical data indicates favourable interaction regions.

It is an object of the invention to address at least one of the problems with the art discussed above.

According to an aspect of the invention, there is provided a method for designing a ligand ab initio that will bind to a binding site of a macro molecular target, or of identifying a modification to a ligand for improving the affinity of the ligand to a binding site of a macro molecular target, comprising:

a) identifying a target list of atoms forming the surface of the target binding site;

b) identifying each atom, hereinafter referred to as a theta atom, in the target list, as a particular theta atom type;

c) extracting from a structural database of biological macromolecules, information about non-bonding, intra-molecular or inter-molecular atom to atom contacts, where the first atom in a contacting pair of atoms is of a particular theta atom type and the opposing, second atom of the pair, hereinafter referred to as an iota atom, is of a particular iota atom type, said information comprising spatial and/or contextual data about the iota atom relative to the theta atom, and said data collected for a plurality of contacts of the given theta atom type from the said database is hereinafter referred to as a theta contact set;

d) for each theta atom identified in the target list in step b), superimposing in or around the target binding site data relating to a given iota atom type, or a predetermined group of related iota atom types, from the corresponding theta contact set extracted in step c);

e) combining and/or parsing the superimposed data in such a way as to predict one or more favoured regions of the binding site where the given iota atom type, or the predetermined group of related iota atom types, has high theoretical propensity; and f) with a candidate ligand notionally docked into the binding site, comparing the type and position of one or more of the atoms of the candidate ligand with the predicted favoured regions for the respective iota atom types, to identify a modification to the candidate ligand, in terms of alternate and/or additional candidate ligand atoms, that will produce a greater intersection between the alternate and/or additional candidate ligand atoms and the respective iota atom type favoured regions, leading to an improvement in the affinity of the modified candidate ligand to the binding site compared to the unmodified candidate ligand;

wherein each non-bonding intra-molecular or inter-molecular contact in the database is defined as a contact between opposing residues of a protein fold or between opposing monomer units of a macromolecular fold or between two interacting macromolecular partners and is specifically between a theta atom on one side of the fold or first interacting partner and an iota atom on the opposing side or second interacting partner; in an instance where the following condition is satisfied:

$s = Rw \leq t$, where s is the separation between the two atoms of the contact, Rw is the sum of the van der Waals radii of the two atoms of the contact, and t is a predetermined threshold distance; and wherein the theta atom type is identified uniquely in step b) such that there is no intersection between the data of a theta contact set extracted in step c) for a given theta atom type and the data of any other theta contact set extracted in step c) for any other theta atom type, apart from data concerning contacts involving the given theta atom as the iota atom.

Thus, each target atom type in the binding site is classified uniquely and is associated with information about a set of contacts extracted from the structural database that is unique and which does not overlap with the set of contacts associated with any other atom type (apart from those contacts which involve the target atom type itself as the iota atom). This means that a distribution of theoretical locations for a given iota atom type, or a predetermined group of related iota atom types, determined based on one target atom in the binding site may be combined (e.g. by summing) more efficiently (e.g. without weighting) with a distribution of theoretical locations for an iota atom type, or predetermined group of related iota atom types, determined based on another target atom in the binding site, for example to provide an improved prediction of one or more favoured regions for the iota atom type or predetermined group of related iota atom types. Also because each target atom in the binding site is classified uniquely, there are no variations in bond lengths or angles to consider and hence the theoretical location of a given iota atom is more precise.

In an embodiment, simple rules are applied to uniquely identify the neighbouring atoms for the purposes of triangulation. No assumptions need to be made about the chemical nature of neighbouring atoms, which is necessary for example where contact types are characterized in terms of the 163 3-atom fragment types of Laskowski et al.

In an embodiment, the spatial data extracted in step c) defines the position of each iota atom specified in the theta contact set by geometrical reference to the position of the theta atom and to the positions of third and fourth atoms, wherein the third atom is covalently bonded to the theta atom and the fourth atom is covalently bonded to the third atom. In an example of such an embodiment, for each iota atom specified in the theta contact set, said spatial data extracted in step c) further defines the position of fifth and sixth atoms by geometrical reference to the position of the theta atom and to the positions of the third and fourth atoms, wherein the fifth atom is covalently bonded to the iota atom and the sixth atom is covalently bonded to either the fifth atom or the iota atom.

In an embodiment, the superimposition in or around the target site of step (d) comprises: parsing the theta contact set to extract spatial data for contacts comprising the given iota atom type or one or more of the predetermined group of related iota atom types; and plotting this spatial data to determine theoretical locations representing where each iota atom type, or each of the one or more of the predetermined group of related iota atom types, would be located if: i) the theta atom of the contact were located at the position of the corresponding theta atom in the target binding site; and ii) the third and fourth atoms of the contact were located at the positions of the third and fourth atoms of the corresponding theta atom in the target binding site. In an embodiment, the spatial data is parsed against the contextual data before the plotting step.

In an embodiment, a region in which a density of theoretical locations for the iota atom type (or one or more of the predetermined groups of related iota atom types) is above a predetermined threshold is identified as one of the favoured regions. In an example of such an embodiment, theoretical locations for the given iota atom type, or for one or more of the predetermined group of related iota atom types, are determined for a plurality of theta atoms on the target list and a region in which a density of the cumulative theoretical locations is above the predetermined threshold is identified as one of the favoured regions.

Thus, theoretical locations are combined cumulatively from different atoms in the binding site before the density of theoretical locations is obtained for the purposes of predicting favoured regions. This results in a more accurate statistical representation of the probability of a given iota atom type, or in a given group of related iota atom types, being positioned at a given location because it takes into account the contributions from all relevant atom types in the binding site in a proportionate and unbiased manner. In Laskowski et al, in contrast, the density functions are derived for groups of 3-atom fragments. Each atom may be associated with several different groups of 3-atom fragments and so it is not possible simply to add together density functions in a manner comparable with embodiments of the present invention. Instead, it is necessary to perform weighting and/or averaging before combining density functions, which increases complexity and/or reduces accuracy.

In an embodiment only contacts between atoms that are separated from each other by four residues or more are used for identifying favoured regions. This significantly reduces or avoids bias due to short range secondary structure. In an embodiment, the contact data predominantly represents long-range, across-fold protein data.

According to a further aspect of the invention, there is provided a method of generating a database for use in a method for designing a ligand ab initio that will bind to a binding site of a macro molecular target, or of identifying a modification to a ligand for improving the affinity of the ligand to a binding site of a macromolecular target, comprising:

analysing the relative positions of atoms in each of a plurality of proteins or other biological macromolecules in order to identify instances of a non-bonding intra-molecular contact between a first atom, referred to as a theta atom, and a second atom, referred to as an iota atom, of the protein or macromolecule; and generating a database that for each identified contact specifies: the type of the theta atom, the type of the iota atom, and the position of the iota atom relative to the theta atom;

wherein a non-bonding intra-molecular contact is defined as an instance where the following conditions are satisfied:

$s=Rw\leq t$ , where s is the separation between the theta and iota atoms, Rw is the sum of the van der Waals radii of the theta and iota atoms, and t is a predetermined threshold distance of typically 2.5 angstroms and preferably 0.8 angstroms; and wherein in the case of proteins, the theta and iota atoms are on amino acid residues separated from each other by at least four residues on a linear polypeptide or are on separate polypeptide chains.

According to a further aspect of the invention, there is provided a method of generating a database for use in a method for designing a ligand ab initio that will bind to a binding site of a macro molecular target, or of identifying a modification to a ligand for improving the affinity of the ligand to a binding site of a macromolecular target, comprising:

analysing the relative positions of atoms in each of a plurality of proteins or other biological macromolecules in order to identify instances of a non-bonding intra-molecular contact between a first atom referred to as a theta atom, and a second atom, referred to as an iota atom, of the protein or macromolecule; and generating a database that for each identified contact specifies: the type of the theta atom, the type of the iota atom, and the position of the iota atom relative to the theta atom;

wherein a non-bonding intra-molecular contact is defined as an instance where the following condition is satisfied:

$s=Rw\leq t$, where s is the separation between the theta and iota atoms, Rw is the sum of the van der Waals radii of the theta and iota atoms, and t is a predetermined threshold distance of typically 2.5 angstroms and preferably 0.8 angstroms; and wherein the method comprises sub-dividing the database to form groups of identified contacts in which the theta atom is one and only one of the 167 non-hydrogen atoms present in the 20 natural amino acids of proteins and the iota atom is in one and only one of a plurality of non-overlapping groups obtained by sorting the 167 non-hydrogen atoms present in the 20 natural amino acids of proteins into groups based on chemical similarity.

Embodiments of the invention will now be described, by way of example only, with reference to the accompanying drawings in which corresponding reference symbols represent corresponding parts, and in which:

FIG. 14 is a flow chart illustrating steps in a method of predicting the effects of point mutations at the VH-VL interface of a Fab;

Figure 1:
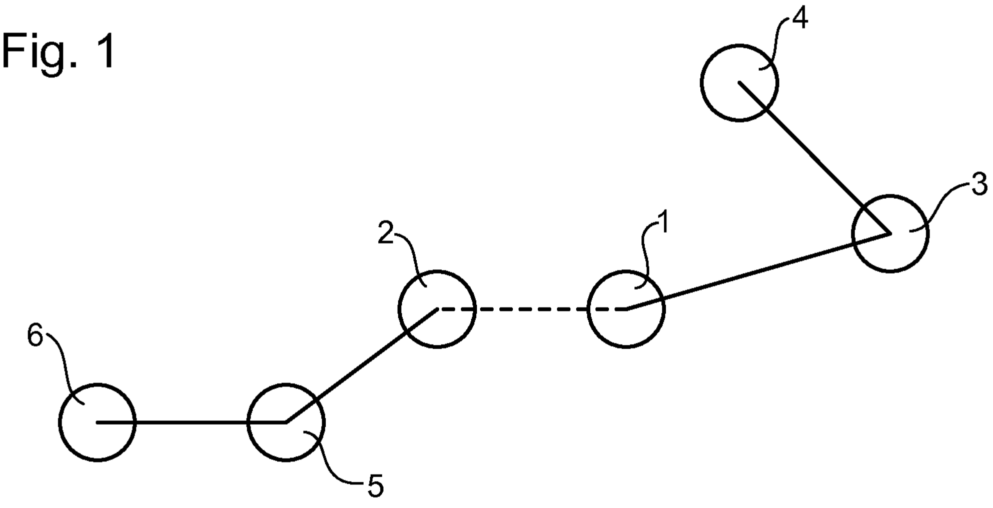
FIG. 1 is a schematic illustration of an example nomenclature for atoms at a non-bonding intra-molecular or intermolecular contact and neighbouring atoms that are used for coordinate normalization.

The Worldwide Protein Data Bank (wwPDB) maintains an archive of macro molecular structural data that is freely and publicly available to the global community. By May 2013 this dataset had reached the milestone of 90 000 structures. Most of these macromolecules are proteins of which the majority have been determined by X-ray crystallography. Deposited data thus contains three dimensional data at the atomic level in the form of Cartesian coordinates of individual atoms that make up the respective protein structure.

The inventors hypothesised that it is possible to extract useful information from this archive which could be applied to aid the design of novel therapeutics. The polypeptide chains of a nascent protein fold into complex three dimensional tertiary and quaternary structures in a remarkably reproducible manner to yield the mature protein. Interactions affecting the formation of the secondary structure of proteins, elements such as helices, beta-sheets and turns, are known. However, rules predicting the higher orders of protein folding are poorly understood. Nonetheless, the inventors have realised that there must be precise rules that govern the interaction of non-bonding but "contacting" atoms, either within the same molecular, for example on opposing faces of a protein fold, or on different molecules.

In an embodiment, a structural database of biological macromolecules (e.g. the wwPDB) is analysed to extract such rules, and the rules are applied to facilitate drug discovery. An example of such a process is described below.

In an embodiment, non-bonding pairs of contact atoms (referred to respectively as "theta" and "iota" atoms) are identified for each macromolecule (e.g. protein), or a sub-set of fewer than all of the macromolecules, in the structural database of macromolecules (e.g. the wwPDB). Such contacts may occur for example between opposing residues of a protein fold or between opposing monomer units of a macro molecular fold (between separate chains of a macromolecular structure) or between two interacting macromolecular partners. Each contact is classified as being between a theta atom on one side of the fold or first interacting partner and an iota atom on the opposing side or second interacting partner.

In an embodiment, the non-bonding intra-molecular or inter-molecular contacts are defined as an instance where the following condition is satisfied: 1) $s-Rw \leq t$, where s is the separation between the two atoms of the contact, Rw is the sum of the van der Waals radii of the two atoms of the contact, and t is a predetermined threshold distance; and, optionally, the following condition also: 2) the two atoms of the contact are separated from each other by at least four residues along a linear polypeptide chain or are on separate polypeptide chains. In an embodiment, the predetermined distance is 2.5 angstroms. In another embodiment, the predetermined distance is 1.5 angstroms. In another embodiment, the predetermined distance is 1.0 angstroms. In another embodiment, the predetermined distance is 0.8 angstroms.

In the description below, any reference to "contact" is understood to mean "non-bonding intra-molecular contact or inter-molecular contact" according to the definition given above.

Databases such as the wwPDB may have information about proteins that are very similar to each other and/or which have related structures. In an embodiment, the database is parsed in order to avoid/reduce bias caused by such similarities/relationships. In an embodiment, the parsing is performed based on primary sequence homology, for example such that only one representative structure of each family of similar/related proteins is selected for analysis. Additionally or alternatively, one or more further selection criteria may be used, for example high resolution and low temperature factor structures may be incorporated.

In an embodiment, a secondary database is constructed starting from the (primary) structural database of biological macromolecules (e.g. the wwPDB). The secondary database comprises information about the non-bonding intra-molecular or inter-molecular contacts. In an embodiment, the secondary database comprises information about more than 1 million contact pairs, optionally more than 5 million contact pairs, optionally more than 11 million contact pairs. In one embodiment, the secondary database comprises information from more than 15 million contact atom pairs, extracted from around 20 000 non-homologous proteins.

In an embodiment, the secondary database contains information about the precise atom types of the contact pair. In an embodiment, the secondary database contains spatial data defining the three dimensional relationship of the theta atom to the iota atom. In an embodiment, the secondary database also contains contextual data concerning the local environment of the contact. In an embodiment, the contextual data contains information concerning the local environment of each contact pair, including one or more of the following in any combination: secondary structure, amino acid types or other monomer types comprising the contact pair, adjacent monomer units and/or local geometry thereof in a polymer chain either side of the contact, adjacent amino acids in a polypeptide chain on either side of the contact, local geometry of the said adjacent monomer units or amino acids, temperature factor of the theta atom, temperature factor of the iota atom, accessible surface area of the theta atom, accessible surface area of the iota atom, the number of different iota atom contacts for the particular theta atom and the number of other theta atoms on the same monomer unit as the theta atom.

In an embodiment, the 3-D coordinates of the contact pair and covalently attached adjacent atoms are normalized, as a group, to a common database reference frame as described below. This simplifies subsequent analysis of potential underlying contact patterns or rules and application of any such rules to drug design.

In an embodiment, the theta atom type is identified as being one and only one of: the 167 covalent atom types (excluding hydrogen) that make up the 20 natural amino acid building blocks of proteins (in this case the secondary database may be divided accordingly and comprise information about up to 27889, 167×167, different contact types); and/or the 82 non-hydrogen atoms present in the 4 nucleotides of the deoxyribonucleic acid polymer (DNA); and/or the 42 non-hydrogen atoms present in the methylated DNA nucleotides, cytidine phosphate and adenosine phosphate; and/or the 85 non-hydrogen atoms present in the 4 nucleotide phosphates of the ribonucleic acid polymer (RNA); and/or the 89 non-hydrogen atoms present in 2-0'- methylated ribose nucleotide phosphates of RNA; and/or the over 400 non-hydrogen atoms present in the commonest post-transcription base modified RNA.

In an embodiment, the iota atom type is identified as being one and only one of: the 167 covalent atom types (excluding hydrogen) that make up the 20 natural amino acid building blocks of proteins; and/or the oxygen atom present in protein bound, structurally relevant, water molecules (this may be useful because crystal structures in the primary database often contain structurally relevant water molecules, i.e. certain protein atoms show definite interactions with bound water molecules); and/or the 82 non-hydrogen atoms present in the 4 nucleotides of the deoxyribonucleic acid polymer (DNA); and/or the 42 non-hydrogen atoms present in the methylated DNA nucleotides, cytidine phosphate and adenosine phosphate; and/or the 85 non-hydrogen atoms present in the 4 nucleotide phosphates of the ribonucleic acid polymer (RNA); and/or the 89 non-hydrogen atoms present in 2-0'methylated ribose nucleotide phosphates of RNA; and/or the over 400 non-hydrogen atoms present in the commonest post-transcription base modified RNA.

In a contact pair the opposing atom is viewed and recorded from either side on the contact. The nomenclature in an example embodiment is described below and illustrated schematically in FIG. 1.

The atom on the reference side of the contact is termed the theta atom 1 whilst the opposing atom is termed the iota atom 2. In this example, the further atoms used for normalizing the 3-D coordinates are defined as follows. The next atom to which the theta atom 1 is covalently bonded, in the direction of the C alpha atom of that amino acid, is referred to as the third atom 3 and the next atom again, the fourth atom 4. The fourth atom 4 is covalently bonded to the third atom 3. The next atom to which the iota atom 2 is covalently bonded, in the direction of the C alpha atom of the respective amino acid, is termed the fifth atom 5 and the next again atom, the sixth atom 6. The sixth atom is covalently bonding to either the fifth atom or the iota atom 2.

In an embodiment, to avoid instances of ambiguity the third and fourth atoms are chosen uniquely for each specified theta atom type. In an embodiment, the fifth and sixth atoms are also chosen uniquely. In an embodiment, the following convention is applied. If the theta atom 1 happens to be a C alpha atom, then the third and fourth atoms are the backbone carbonyl carbon and oxygen atoms respectively. If the theta atom 1 is a backbone carbonyl carbon, then the third atom 3 and the fourth atom 4 are the C alpha carbon and the backbone nitrogen respectively. If the theta atom 1 is the backbone nitrogen, then the third atom 3 and the fourth atom 4 are the C alpha carbon and the backbone carbonyl carbon respectively. If the theta atom 1 is a C beta carbon atom, then the third atom 3 and the fourth atom 4 are the C alpha carbon and the backbone carbonyl carbon respectively. In phenylalanine and tyrosine side chains where there is a choice of two epsilon carbon atoms for the third and fourth atom positions, then the atom closest to the backbone nitrogen atom is selected.

In an embodiment, coordinate normalisation of each contact is performed on the theta, iota, third and fourth atoms, optionally also the fifth and sixth atoms, as a group so that their 3-D relationship is maintained. The resulting normalized coordinates may be referred to as a normalized coordinate group. In an embodiment, this is achieved by carrying out the following steps in sequence, as illustrated in FIGS. 2-6.

Figure 2:
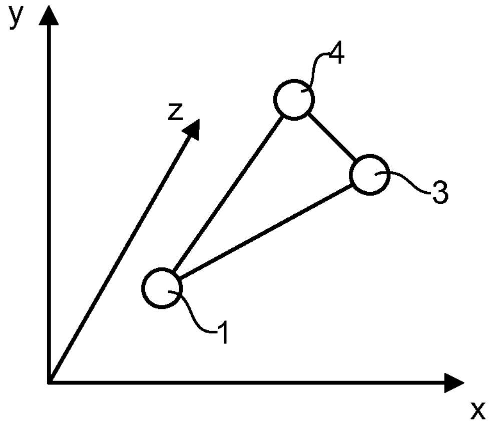
FIGS. 2-6 illustrate a process of coordinate normalization for an atom in a non-bonding intra-molecular or intermolecular contact.
Figure 3:
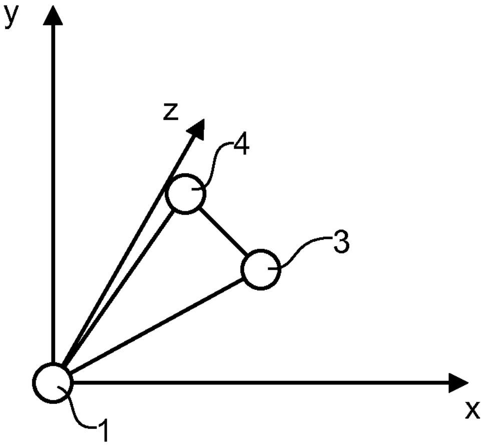
Figure 4:
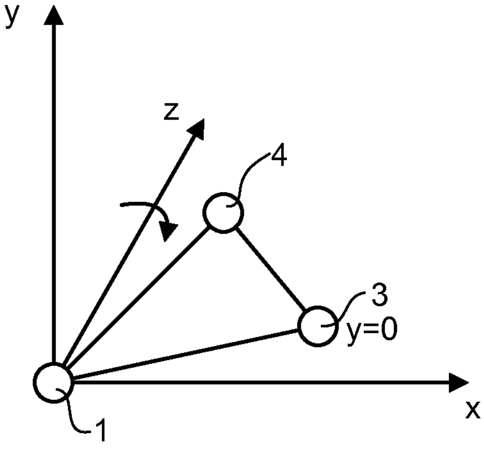
Figure 5:
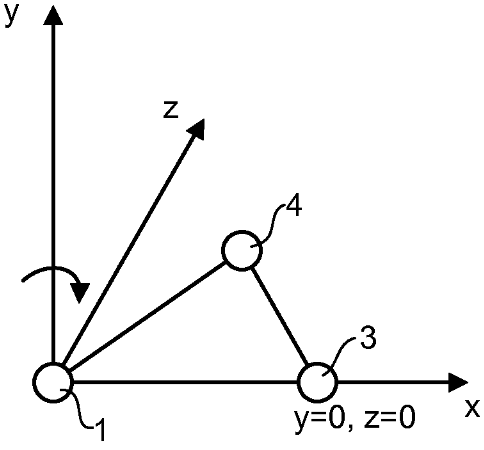
Figure 6:
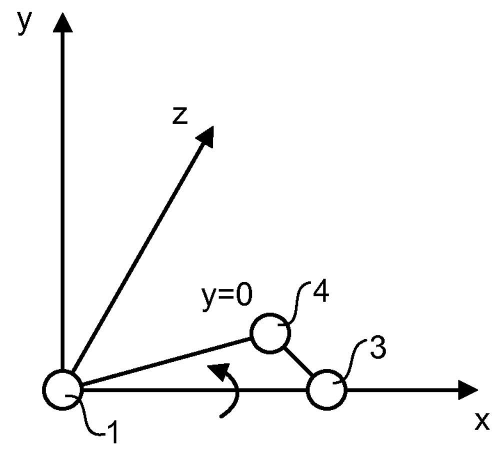

FIG. 2 illustrates a theta atom 1, third atom 3 and fourth atom 4 of a non-bonding intra-molecular or inter-molecular contact positioned relative to a reference frame, defined relative to x-, y- and z-axes, according to coordinates given in a primary database (such as the wwPDB). In a first step of an example coordinate normalization process, the atom group coordinates are translated so that the theta atom 1 lies at the zero coordinate (FIG. 3). Next, the group as a whole is rotated about the z-axis until the third atom 3 is at y=0 (FIG. 4). Next, the group is rotated about the y-axis until the third atom is at y=0 and z=0 (FIG. 5). Next, the group is rotated about the x-axis until the fourth atom 4 is at y=0 and the group as a whole lies in the x-y plane (all three atoms at y=0; FIG. 6). In this manner each of the 167 first atom types can be superimposed for that type and the secondary database sub-divided accordingly. In turn each of the first atom divisions can be sub-divided into 167 iota atom types, facilitating the analysis of the spatial distribution of each iota atom type relative to each theta atom type.

In an embodiment, the distribution patterns of iota atoms relative to theta atoms are analysed in order to identify similarities between the distribution patterns for nominally different iota atom types. In this way, the unique iota atom types (e.g. the 167 covalent atom types mentioned above) can be combined into a number of groups (herein referred to as "predetermined groups of related iota atom types") to simplify subsequent use of the data. Grouping together the atom types according to the similarity of distribution patterns reduces the computational load associated with the method described below with reference to FIG. 7 for example, thus increasing speed and/or reducing hardware expense.

In an embodiment, this process is simplified by using polar coordinates rather than Cartesian coordinates (in an embodiment, this is achieved by performing conversion processing between Cartesian coordinates and polar coordinates, for example where the data in the primary database is presented using Cartesian coordinates). In an embodiment, two-dimensional polar coordinates are used, specifying the relative positions of the theta and iota atoms in terms only of the two polar angles Θ (theta) and φ (phi) (corresponding to latitude and longitude on a globe). The resulting two-dimensional latitude-longitude plots do not show any information about variations in the distance between the theta and iota atoms. However, it is found that this distance is relatively constant, so that the theta-phi plots contain most of the relevant information concerning the contact. Reducing the analysis to a problem in two dimensions rather than three greatly improves the efficiency of subsequent analyses. In an embodiment, contour lines are used to illustrate variations in the relative position of the iota atom. The contour lines may represent lines of constant "density" or probability of a relative positioning of the theta and iota atoms.

Analysis of such polar angle plots has revealed that a particularly important factor governing the pattern of iota atom frequencies is the elemental nature and hybridisation state of the iota atoms, i.e. C sp3 , C sp2(aromatic), C sp2(non-aromatic), N sp3 , N sp2, O sp3 , O sp2 or S. As a result, it is possible to improve analysis efficiency by grouping the 167 atom types according to these identified eight groups. In other embodiments, a different grouping may be used.

In general, environmental factors around the contact, such as the nature of adjacent amino acids, make less difference to the iota frequency pattern, with the exception of secondary structure. As might be expected the frequency patterns of backbone amide nitrogen theta atoms versus backbone oxygen iota atoms and vice-versa are skewed by secondary structure, in particular as regards whether or not they are from beta sheet.

In an embodiment, the secondary database tags contact data with the local secondary structure type (helix, beta sheet or random coil). This provides the basis for differentiating any potential influence of secondary structure on contact patterns at a later stage.

In an embodiment, a method is provided based on the above that assists with the identification of modifications to a ligand that improve the strength of binding, or affinity, of the ligand to a binding site. In an embodiment, the method is used to assist with NCE or biologic drug design. In respect of the former, the method may be useful for predicting 'hotspots' or pharmacophore atom positions in potential drug binding sites of target proteins. This can facilitate de novo drug design. In situations where there is an available structure of chemical matter bound in a binding site, the method can suggest atom types and positions for elaboration of the chemistry to obtain a ligand with better binding characteristics. In the case of protein drugs such antibodies, the method may be used to predict mutations in the protein or antibody binding site that would lead to improvement in binding affinity or specificity. The method may also be used to suggest positions for modification within a macromolecular structure to improve the properties of the macromolecule. For example, as illustrated in the Examples section below, the method may be used to identify point mutations within antibody VH and VL chains in order to improve the thermal stability of the antibody. The mutations are on separate chains, but are still within the antibody macromolecule.

Figure 7:
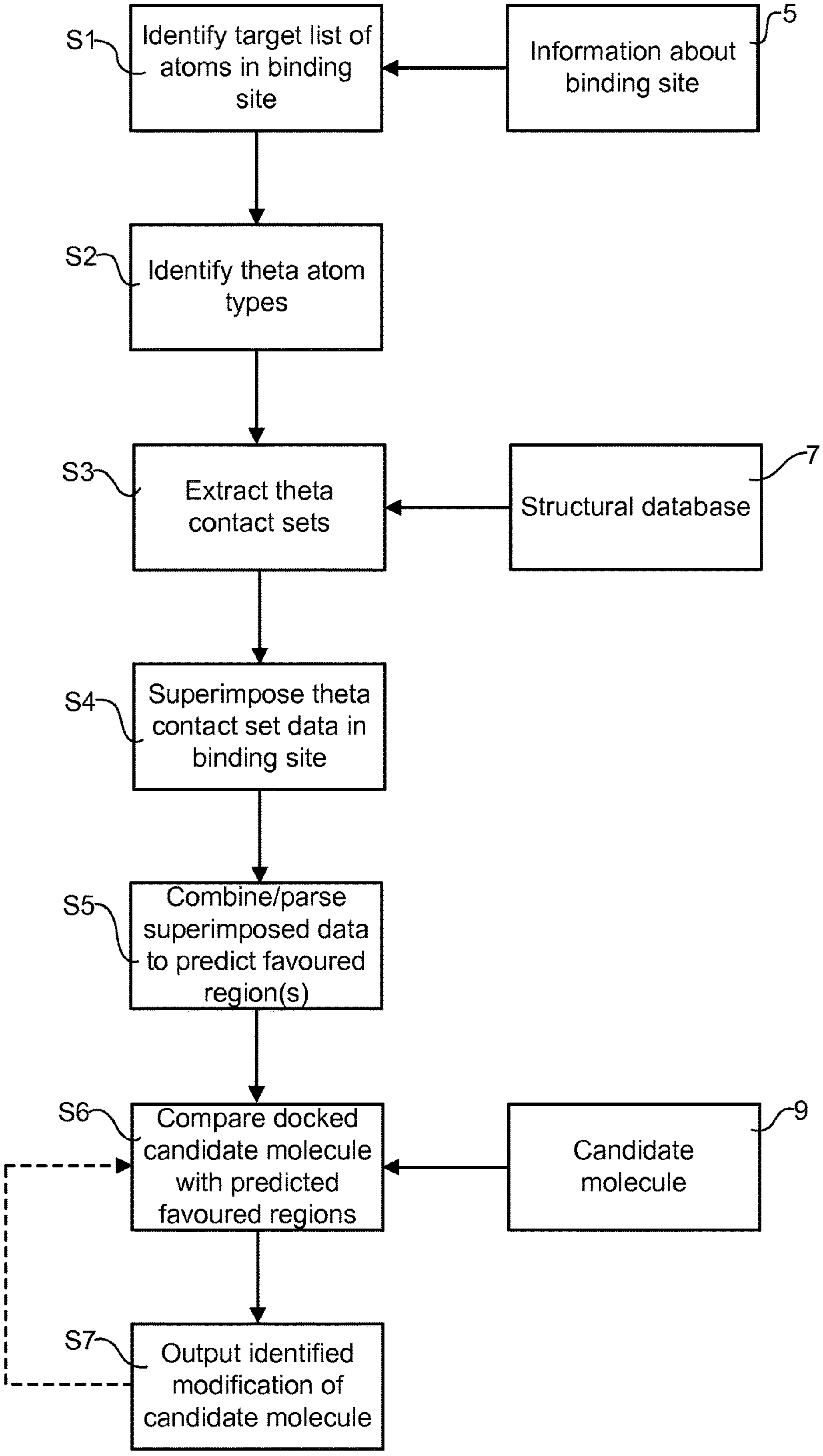
FIG. 7 is a flow chart illustrating steps in a method of designing a ligand ab initio that will bind to a binding site of a macro molecular target, or of identifying a modification to a ligand for improving the affinity of the ligand to a binding site of a macro molecular target.

FIG. 7 illustrates an example method for designing a ligand ab initio that will bind to a binding site of a macromolecular target, or of identifying a modification to a ligand for improving the affinity of the ligand to a binding site of a macromolecular target.

In step S1, data representing the target binding site of a target protein is obtained, for example from a local or remote memory device 5. A target list of atoms forming the surface of the target binding site is identified.

In step S2, each atom in the target list is identified as a particular theta atom type.

In step S3, information is extracted from a structural database of biological macromolecules (e.g. the wwPDB), provided for example by a local or remote memory device 7, about non-bonding, intra-molecular or inter-molecular contacts in which the first atom in a contacting pair of atoms is a particular theta atom type and the opposing, second atom of the pair is a particular iota atom type. The extracted information comprises spatial and/or contextual data about the iota atom relative to the theta atom. The data is collected for a plurality of contacts of the given theta atom type and the resulting set of data is referred to as a theta contact set. In an embodiment, the theta contact set comprises data collected for all of the available contacts of the given theta atom type. The extracted information may form a database that is an example of the "secondary database" discussed above. In an embodiment, the information extracted in step S3 is collected in a secondary database that comprises one and only one theta contact set for each of the theta atom types. In an example of such an embodiment, the theta contact sets of the secondary database are subdivided into a plurality of non-overlapping iota atom types or non-overlapping groups of related iota atom types. In an example of such an embodiment, the database is sub-divided to form groups of identified contacts in which the first atom is one and only one of the 167 non-hydrogen atoms present in the 20 natural amino acids of proteins and the second atom is in one and only one of a plurality of non-overlapping groups obtained by sorting the 167 non-hydrogen atoms present in the 20 natural amino acids of proteins into groups based on chemical similarity.

In step S4, for each theta atom identified in the target list in step S2, data relating to a given iota atom type, or a predetermined group of related iota atom types, from the corresponding theta contact set extracted in step S3 is superimposed in or around the target binding site. In an embodiment, the superimposition comprises: parsing the theta contact set to extract spatial data for contacts comprising the given iota atom type or one or more of the predetermined group of related iota atom types; and plotting this spatial data to determine theoretical locations representing where each iota atom type, or each of the one or more of the predetermined group of related iota atom types, would be located if: i) the theta atom of the contact were located at the position of the corresponding theta atom in the target binding site; and ii) the third and fourth atoms of the contact were located at the positions of the third and fourth atoms of the corresponding theta atom in the target binding site. Where determined theoretical locations conflict with binding site atoms and/or are buried within the target protein, these may be removed from further analysis. For example if it is determined that the theoretical location of an individual iota atom intersects with the location of an atom of the target macromolecule closer than Rw−0.2 angstroms then the iota atom is excluded from subsequent analysis.

In step S5, the superimposed data is combined and/or parsed in such a way as to predict one or more favoured regions of the binding site where the given iota type, or the predetermined group of related iota atom types, has high theoretical propensity.

In step S6, a candidate ligand is notionally docked into the binding site. Data defining the candidate ligand may be provided for example from a local or remote memory device 9. A comparison is then made between the type and position of one or more of the atoms of the candidate ligand with the predicted favoured regions for the respective iota atom types. On the basis of the comparison, modifications to the candidate ligand, in terms of alternate or additional candidate ligand atoms, are identified that will produce a greater intersection between the alternate and/or additional candidate ligand atoms and the respective iota atom type favoured regions, leading to an improvement in the affinity of the modified candidate ligand to the binding site compared to the unmodified candidate ligand.

In step S7, the modified candidate ligand is output either as a proposed improvement to an existing ligand or as part of an ab initio design of a new ligand. Optionally steps S7 and S6 can be iterated to further modify the ligand. The local or remote memory devices 5, 7 and 9 may be implemented in a single piece of hardware (e.g. a single storage device) or in two or more different, separate devices.

In an embodiment, the modified candidate ligand is output to an output memory device for storage or transmission and/or to a display for visualization.

In an embodiment, the type of a given theta atom is identified uniquely in step S2 such that there is no intersection between the group of contacts for which information is extracted in step S3 for the given theta atom and the group of contacts for any other theta atom type (with the exception of contacts involving the given theta atom type as the iota atom).

In an embodiment, step S5 comprises determining one or more favoured regions for each of a plurality of different iota atom types and/or predetermined groups of related iota atom types. In such an embodiment, the comparison step S6 may be repeated for each of the plurality of different iota atom types and/or predetermined groups of related iota atom types, in order to identify potential modifications that involve the different iota atoms types or predetermined groups of related iota atom types.

In an embodiment, steps S2-S7 are performed for a plurality of different atoms in the binding site. In an embodiment, as described below, favoured regions may be determined more accurately by cumulatively combining (e.g. summing) the distributions of determined theoretical locations of the iota atom types as derived for a plurality of different atoms in the binding site.

In an embodiment, the analysis is extended such that, for each favoured region, vectors are derived that describe the position of the fifth atom relative to its respective iota atom. Analysis is carried out on the vectors to identify a favoured bond vector representing a prediction of the covalent attachment of a theoretical consensus iota atom in the region. The identified favoured bond vector can then be used to refine the design of the candidate ligand and/or to refine the modification of the candidate ligand, as applicable. The identified favoured bond vector may be used for example to indicate how iota atoms in different favoured regions might be bonded together, thus assisting with the identification of modifications involving plural additions or exchanges of atoms. In an embodiment the analysis is a cluster analysis.

The distribution of theoretical locations gives a measure or propensity of how a particular iota atom type (or predetermined group of related iota atom types) will be favoured at different locations in the binding site. In an embodiment, a region in which a density of the theoretical locations is above a predetermined threshold is identified as one of the favoured regions. The density of theoretical locations is a measure of the number of determined theoretical locations that occur in a given spatial volume for example. In an embodiment, iota atom theoretical locations are determined for a plurality of target atoms in the binding site and a region in which a density of the cumulative theoretical locations for the iota atom (or predetermined group of related iota atom types) for the plurality of target atoms is above the predetermined threshold is identified as one of the favoured regions. The theoretical locations determined for different target atoms in the binding site may be summed, for example, in order to obtain the cumulative theoretical locations. This approach to taking into account the effects of different atoms in the binding site is computationally efficient and minimizes loss of information about the interaction between the candidate ligand and the binding site. The approach is facilitated by the characterization of contacts in terms of pairs of simple atom types or simple atom types in combination with atoms of predetermined groups of simple atom types. Such an approach is not valid when contacts are characterized in terms of 3-atom fragments, such as is the case in Laskowski et al. for example.

The obtained distributions of theoretical locations can be transformed in various ways to create probability density functions, i.e. a statistical potential for the preference of a given iota atom type at a given position in the binding site. In turn, probability density functions can be treated in an analogous way to electron density and converted into ccp4 files which are a standard way of visualising such maps within molecular graphics software, e.g. Pymol.

In an embodiment, in step S5, the one or more favoured regions is/are expressed in polar coordinates, optionally comprising only the polar and azimuthal angles, optionally wherein the reference frame is normalized by reference to the third and fourth atoms 3,4.

In an embodiment, step S6 comprises: identifying a modification of the candidate ligand that increases a degree of overlap between an atom of the candidate ligand (whether present before the modification or not) and a predicted favoured region for an atom of the same type in the binding site. In an embodiment, the generated distributions of theoretical locations and/or favoured regions are inspected, for example by computer software or manually, as superimpositions on the target macromolecular structure in complex with the respective candidate ligand. If for instance the candidate ligand relates to an antibody, the interface between the antibody and target macromolecule may be examined to determine the degree of overlap between antibody atoms and the respective iota atom theoretical location distributions and/or favoured regions identified for that atom. In some cases the degree of overlap will already be high. However, in other regions of the interface the overlap may be low. It is in these regions where mutations in the adjacent amino acid residue of the antibody may be most effectively identified/proposed. In an embodiment each of the 19 other natural amino acids is considered in turn at this position, in all of their respective rotamer conformations and in each case the degree of overlap with the relevant iota atom theoretical location distributions and/or favoured regions is examined, with the aim of selecting those residues with the maximum degree of overlap for proposed mutations. In this manner, a rational means of selecting mutations is provided that may generate affinity improvements in the chosen antibody. Individual point mutations in different regions of the antibody-target protein interface may be generated; those that lead to affinity improvement can be tested in combinations of two or more that may give synergistic increases in affinity.

In an embodiment, step S6 comprises replacing each of one or more of (optionally all of) the amino acid residues of the ligand that is/are in direct contact with the target binding site, or in close proximity to the target binding site, with each of one or more of (optionally all of) the residues chosen from the other 19 natural amino acids. Each such replacement, is referred to herein as a "residue replacement" and involves the modification of a ligand by a single replacement of one residue with a different residue. In an embodiment, for each such residue replacement that does not cause conflict with adjacent atoms of the ligand or target (e.g overlap between one or more atoms of the replacement residue and one or more other atoms of the target or ligand), the type and position of each atom of the replacement residue is compared with the respective iota atom type favoured regions to identify whether they will produce a greater intersection than the atoms of the original residue. In an embodiment a list is then output of the residue replacements that are identified as producing a greater intersection than atoms of the original residue. In an embodiment, for each of the listed residue replacements, the candidate ligand is then mutated to produce a modified, single-residue-mutated ligand that incorporates the residue replacement. The affinity of each modified ligand to the target binding site can then be tested by experiment in order to identify those modifications which provide the greatest affinity improvement for the candidate ligand. For example, a group of residue replacements may be identified that yield a residue replacement that is greater than a predetermined threshold. In an embodiment, the predetermined threshold may be zero so that the selected group consists only of residue replacements that improve the affinity to some extent. More advanced modifications of the candidate ligand can then be carried out based on this information. For example, in an embodiment the candidate ligand may be modified to incorporate a plurality of residue replacements, for example a plurality of those residue replacements that, individually, were determined as providing the greatest affinity improvements. In this way it is possible to design a ligand that has an affinity that is improved even more than is possible by replacing only a single residue.

In some embodiments, lists of residue replacements may be produced that satisfy providing a greater intersection than atoms of the original residue (have a AIOTAscore of less than zero). The lists may additionally be ranked based on other criteria. For example, lists may also be filtered based on $\Delta\Delta G$ scores (see below). Residue replacements withAAG scores of less than zero imply stronger interactions compared with the original residue. Therefore a list may be produced where residues satisfy both criteria of a AIOTAscore of less than zero (a negative AIOTAscore), and a $\Delta\Delta G$ of less than zero (a negative $\Delta\Delta G$). This is illustrated in Example 2 below.

In the case of chemical matter, for instance a crystal structure of a low molecular weight chemical fragment bound in a pocket of a target protein, iota atom theoretical location distributions and/or favoured regions displayed in the binding site may suggest atom types and vectors of chemical bonds for fragment growth that may yield a prototype NCE of higher potency.

In an embodiment, a plurality of modifications to the candidate ligand are identified. In this case, the method may further comprise selecting a subset of the identified modifications, for example to identify the modifications which are likely to be most effective in terms of improving affinity. The selection may be carried out based on the extent to which the intersection between the alternate and/or additional candidate ligand atoms and the respective iota atom type favoured regions is greater compared to the unmodified candidate ligand. For example, modifications that result in an increase in the intersection that is above a predetermined threshold may be selected and modifications that result in an increase in the intersection that is below a predetermined threshold may be discarded. An example of such a selection process is discussed below in the context of "Example 2". The 'AIOTAScore" is an example of a measure of the extent to which the intersection between the alternate and/or additional candidate ligand atoms and the respective iota atom type favoured regions is greater compared to the unmodified candidate ligand. Alternatively or additionally, the selection may be carried out based on the extent to which one or more factors contributing to the total energy of the complex formed by the binding of the modified candidate ligand to the binding site is/are reduced compared to the case where the unmodified candidate ligand is bound. For example, modifications that result in a decrease in the one or more factors (e.g. a decrease in a sum of the one or more factors) that is above a predetermined threshold may be selected and modifications that result in a decrease in the one or more factors (e.g. a decrease in a sum of the one or more factors) that is below a predetermined threshold may be discarded. An example of such a selection process is discussed below in the context of "Example 2". The "Rosetta ΔΔG score" is an example of a measure of the extent to which one or more factors contributing to the total energy of the complex formed by the binding of the candidate ligand to the binding site is/are reduced. Examples of factors contributing to the total energy of the complex include a Lennard-Jones term, an implicit solvation term, an orientation-dependent hydrogen bond term, sidechain and backbone torsion potentials derived from the PDB, a short-ranged knowledge-based electrostatic term, and reference energies for each of the 20 amino acids that model the unfolded state, as discussed below.

In an embodiment, the method of identifying a modification to a candidate ligand is a computer-implemented method. In an embodiment, any one or more of the steps S1-S7 is/are performed on a computer. In an embodiment, all of the steps S1-S7 is/are performed on a computer. In addition, any one or more of the steps S101-S109 of FIG. 14 (illustrating a workflow for predicting point mutations at the VH-VL interface of an antibody) may be automated. Any one or more of the steps S101-S109 may be performed on a computer. In one embodiment, all of the steps S101-S109 are automated. All of the steps S101-S109 may be performed on a computer.

A wide range of standard computing configurations, well known to the person skilled in the art, could be used as platforms to implement the method. The method is not limited to any particular hardware configuration, operating system or means for storing or transmitting software necessary for defining and/or implementing the method steps. In an embodiment, a computer readable medium or signal is provided that comprises computer readable instructions (e.g. code in a computer programming language) for causing a computer to carry out the method.

In an embodiment, a method of manufacturing a therapeutic ligand is provided. In an embodiment, the method of manufacturing comprises designing a new ligand or modifying an existing ligand according to one or more of the embodiments described above.

EXAMPLE 1

Affinity Maturation of a Fab Fragment of an Anti-IL17F Antibody

Introduction

In vitro methods of antibody affinity maturation are well known (see U.S. Pat. No. 8,303,953 B2 column 13 lines 19 to 33). In a recent example Fujino et al (Fujino et al (2012) "Robust in vitro affinity maturation strategy based on interface-focused high-throughput mutationalscanning", Biochem. Biophys. Res. Comm., 428, 395-400) report a high throughput mutational scanning strategy based on ribosome display panning of single point mutant single-chain Fab libraries at each of 50 identified antigen interface residues of the antibody, followed combinatorial ribosome display of enhanced binders that resulted in identification of a Fab with over 2000-fold affinity improvement. Such methods require a large investment in laboratory based resources and therefore various groups (reviewed by Kuroda et al (2012) "Computer-aided antibody design", Prot. Eng. Design & Selection, 25, 507-521) have investigated in silico methods that predict improvements in antibody affinity so as to reduce or eliminate the need for screening large numbers of mutated antibody variants for improved affinity. These computer-aided antibody design protocols are either knowledge-based; i.e. using statistical potentials derived from observational data or physics-based, i.e. using and energy functions derived from models of the underlying physical interactions. Lippow et al (2007) (Lippow et al (2007), "Computational design of antibody-affinity improvement beyond in vivo maturation", Nat Biotech., 25, 1171-1176) have achieved moderate success with the latter approach based on electrostatic interactions, but our understanding of parameterisation of such methods is still far from complete. Knowledge-based methods to date tend to identify individual antibody residues for random mutagenesis (e.g. Barderas et al (2008) "Affinity maturation of antibodies assisted by in silico modelling", PNAS, 105, 9029-9034), which still entail considerable laboratory based effort.

In this Example, a knowledge-based approach was applied to affinity mature a Fab fragment of the anti-IL17F antibody described in U.S. Pat. No. 8,303,953 B2. The final affinity matured antibody is described in WO 2012/095662 A1 as a full length IgG1 molecule. However, the method by which this antibody was affinity matured is not disclosed in the latter publication.

Methods

Identification of Target (Theta) Atoms Comprising the IL17F Epitope

Using the coordinates of the co-crystal IL17F/Fab 496 complex structure described in WO 2009/130459 A2, all IL 17F atoms within 6 A of any Fab 496 atom were identified as epitope atoms and are listed in Table 1. Of this list of 209 theta atoms there are 86 specific theta atom types.

TABLE 1

List of atoms comprising the IL17F epitope where the notation (1)-(2)-(3)-(4) designates (I) the respective F and I chains of the IL17 homodimer, (2) the amino acid residue and (3) residue number and (4) the atom type.

| | | | |
|---|---|---|---|
| F-ASN-53-CG | F-ASN-89-C | F-ILE-129-CA | I-VAL-38-N |
| F-ASN-53-OD1 | F-ASN-89-CA | F-ILE-129-CB | I-VAL-38-0 |
| F-ALA-70-C | F-ASN-89-CB | F-ILE-129-CD1 | I-SER-39-C |
| F-ALA-70-O | F-ASN-89-CG | F-ILE-129-CG1 | I-SER-39-CA |
| F-GLN-71-C | F-ASN-89-N | F-ILE-129-CG2 | I-SER-39-CB |
| F-GLN-71-CA | F-ASN-89-ND2 | F-ILE-129-N | I-SER-39-N |
| F-GLN-71-CB | F-ASN-89-OD1 | F-ILE-129-0 | I-SER-39-OG |
| F-GLN-71-CD | F-SER-90-C | F-HIS-130-C | I-MET-40-C |
| F-GLN-71-CG | F-SER-90-CA | F-HIS-130-N | I-MET-40-N |
| F-GLN-71-N | F-SER-90-CB | F-HIS-130-O | I-MET-40-O |
| F-GLN-71-NE2 | F-SER-90-N | F-HIS-131-C | I-SER-41-C |
| F-GLN-71-0 | F-SER-90-O | F-HIS-131-CA | I-SER-41-CA |
| F-GLN-71-0E1 | F-SER-90-OG | F-HIS-131-CE1 | I-SER-41-CB |
| F-CYS-72-C | F-VAL-91-C | F-HIS-131-N | I-SER-41-N |
| F-CYS-72-CA | F-VAL-91-CA | F-HIS-131-ND1 | I-SER-41-0 |
| F-CYS-72-CB | F-VAL-91-CB | F-HIS-131-0 | I-SER-41-0G |
| F-CYS-72-N | F-VAL-91-CG1 | F-VAL-132-C | I-ARG-42-C |
| F-CYS-72-0 | F-VAL-91-CG2 | F-VAL-132-CA | I-ARG-42-CA |
| F-CYS-72-SG | F-VAL-91-N | F-VAL-132-CB | I-ARG-42-CB |
| F-ARG-73-C | F-VAL-91-0 | F-VAL-132-CG1 | I-ARG-42-CD |
| F-ARG-73-CA | F-PRO-92-C | F-VAL-132-CG2 | I-ARG-42-CG |
| F-ARG-73-CB | F-PRO-92-CA | F-VAL-132-N | I-ARG-42-CZ |
| F-ARG-73-CG | F-PRO-92-CB | F-VAL-132-0 | I-ARG-42-N |
| F-ARG-73-N | F-PRO-92-CD | F-GLN-133-C | I-ARG-42-NE |
| F-ARG-73-0 | F-PRO-92-CG | F-GLN-133-CA | I-ARG-42-NH1 |
| F-ASN-74-C | F-PRO-92-N | F-GLN-133-CB | I-ARG-42-NH2 |
| F-ASN-74-CA | F-PRO-92-0 | F-GLN-133-CD | I-ARG-42-0 |
| F-ASN-74-CB | F-GLN-94-CD | F-GLN-133-CG | I-ASN-43-N |
| F-ASN-74-CG | F-GLN-94-NE2 | F-GLN-133-N | I-ASN-43-OD1 |
| F-ASN-74-N | F-GLN-94-OE1 | F-GLN-133-0 | I-ILE-44-CA |
| F-ASN-74-ND2 | F-GLU-114-0E1 | F-GLN-133-OE1 | I-ILE-44-CB |
| F-ASN-74-0 | F-LEU-117-CB | F-GLN-133-OXT | I-ILE-44-CD1 |
| F-LEU-75-C | F-LEU-117-CD1 | I-ILE-32-CG2 | I-ILE-44-CG1 |
| F-LEU-75-CA | F-LEU-117-CD2 | I-ASN-33-CB | I-ILE-44-CG2 |
| F-LEU-75-CB | F-LEU-117-CG | I-ASN-33-CG | I-ARG-47-CD |
| F-LEU-75-CD1 | F-THR-119-CB | I-ASN-33-ND2 | I-ARG-47-CZ |
| F-LEU-75-CD2 | F-THR-119-CG2 | I-ASN-33-OD1 | I-ARG-47-NE |
| F-LEU-75-CG | F-THR-119-0G1 | I-GLN-36-C | I-ARG-47-NH1 |
| F-LEU-75-N | F-VAL-125-CB | I-GLN-36-CA | I-ARG-47-NH |
| F-LEU-75-0 | F-VAL-125-CG1 | I-GLN-36-CB | |
| F-GLU-84-OE1 | F-VAL-125-CG2 | I-GLN-36-CD | |
| F-ILE-86-C | F-PRO-127-C | I-GLN-36-NE2 | |
| F-ILE-86-CA | F-PRO-127-CA | I-GLN-36-OE1 | |
| F-ILE-86-CB | F-PRO-127-CB | I-ARG-37-C | |
| F-ILE-86-CD1 | F-PRO-127-CD | I-ARG-37-CA | |
| F-ILE-86-CG1 | F-PRO-127-CG | I-ARG-37-CB | |
| F-ILE-86-CG2 | F-PRO-127-N | I-ARG-37-CD | |
| F-ILE-86-0 | F-PRO-127-0 | I-ARG-37-CG | |
| F-SER-87-C | F-VAL-128-C | I-ARG-37-CZ | |
| F-SER-87-CA | F-VAL-128-CA | I-ARG-37-N | |
| F-SER-87-N | F-VAL-128-CB | I-ARG-37-NE | |
| F-SER-87-0 | F-VAL-128-CG1 | I-ARG-37-NH1 | |
| F-MET-88-C | F-VAL-128-CG2 | I-ARG-37-NH2 | |
| F-MET-88-CA | F-VAL-128-N | I-ARG-37-0 | |
| F-MET-88-N | F-VAL-128-0 | I-VAL-38-C | |
| F-MET-88-0 | F-ILE-129-C | I-VAL-38-CA | |

Creation of IOTA Database

A secondary database of over 11 million intra-molecular atomic contact data was extracted from over 20000 non-homologous protein structures where resolution was ≤2 A. Contacts were defined as any two atoms on opposing sides of a protein fold separated by a distance of 1A +the sum of their respective Van der Waals radii or less, and were limited to atoms on residues at least 4 residues apart on the linear peptide sequence. The first atom of the contacting pair was designated the theta atom and the second atom, the iota atom. The database was divided into 167 contact sets according to the theta atom type, there being 167 non-hydrogen atom types within the 20 natural amino acid residues comprising proteins. Within a contact set the relative coordinates of each iota atom position was recorded after normalisation of the theta-iota atom pair coordinates. The latter was achieved by setting the theta atom to x,y,z=0, 0,0; the next covalently attached atom ($3^{rd}$ atom) to the theta atom (in the direction of the peptide backbone) to x,y,z=x', 0,0 and the next again covalently attached atom ($4^{th}$ atom) to x,y,z=x",0,z'. A consistent convention was employed to defined $3^{rd}$ and $4^{th}$ atoms.

Each theta contact set was further sub-divided into 167 iota atom types, but for convenience these were concatenated into 26 sub-groups according to chemical type based on the definition of Engh and Huber (Engh and Huber (1991) "Accurate Bond and Angle Parameters for X-ray Protein Structure Refinement", Acta Cryst., A47, 392-400).

In this Example the following iota sub-groups were employed:

| Description | Atoms |
|---|---|
| Carbonyl O | all backbone O, Asn Oδï, Gin Oεï |
| Tetrahedral $CH_2$ | all Cβ 9except Ala, Iie, Thr, Val) Arg C5,Cy, Gin Cy, Glu Cy, Ile Cy1, Lys Cy, C5, Cε, Met Cy |
| Tetrahedral $CH_3$ | Ala Cβ, lie C51, Cy2, Leu C51, C52, Met Cε, Thr Cy2, Val Cy1, Cy2 |
| NH | all backbone N (except Pro), Arg Nε, His Nδ1, Nε2, Trp Nεï |
| Hydroxyl O | Ser Oγ, Thr Oγï, Tyr Oη |
| Carboxyl O | Asp Oδ1, Oδ2, Glu Oε1, Oε2 |
| $NH_2$ | Asn Nδ2, Gln Nε2 |

Superimposition of Iota Data Over the IL17F Epitope Surface

For each of the 209 theta atoms comprising the IL17F epitope, the corresponding theta contact set was selected from the IOTA database and from that, an appropriate iota sub-group was selected e.g. carbonyl oxygen. The relative iota coordinates from this sub-group were transposed relative to the reference frame of the given theta atom of the IL17F epitope (Table 2 illustrates example data). An iota dataset for a given sub-group was thus accumulated over the whole IL17F epitope. In cases where the location of a given iota data point intersected with an atom of IL17F, closer than the sum of their respective Van der Waals radii minus 0.21, then these data points were excluded from the dataset. The process was repeated for all relevant iota sub-groups to produce a series of iota datasets for the IL17F epitope.

TABLE 2

| id | out01:0000098 | out01:0000127 | out01:0000280 | out01:0000282 |
|---|---|---|---|---|
| pdbcode | 16vpA | 16vpA | 1a0pA | 1a0pA |
| res | 2.1 | 2.1 | 2.5 | 2.5 |
| rval | 0.26 | 0.26 | 0.287 | 0.287 |
| org | *Herpes simplex* | *Herpes simplex* | *Escherichia coli* | *Escherichia coli* |
| Tchain | A | A | A | A |
| Taaind | 96 | 235 | 126 | 137 |
| Taanum | 142 | 281 | 145 | 156 |

TABLE 2-continued

| | | | | |
|---|---|---|---|---|
| Taaname | THR | THR | THR | THR |
| Taass | C | E | H | E |
| Taaphi | −135.7 | −129.6 | −87.1 | −105.2 |
| Taapsi | 163.3 | 160 | −34.9 | 174 |
| Tomg | −179.5 | 178.5 | 178.7 | 177.6 |
| Tc1 | 61.3 | 52.2 | 60.5 | 64.4 |
| Tc2 | 999.9 | 999.9 | 999.9 | 999.9 |
| Tc3 | 999.9 | 999.9 | 999.9 | 999.9 |
| Tc4 | 999.9 | 999.9 | 999.9 | 999.9 |
| TUpAA | ALA | LEU | ALA | LEU |
| TDnAA | ARG | VAL | GLY | MET |
| Tnum | 724 | 1867 | 1032 | 1111 |
| Tname | C | C | C | C |
| Tbval | 23.52 | 24.07 | 31.8 | 38.02 |
| Tasa | 0 | 0 | 0 | 0 |
| Tcdist | 0 | 0 | 0 | 0 |
| Todist | 1.234 | 1.233 | 1.215 | 1.239 |
| Tndist | 2.463 | 2.461 | 2.482 | 2.455 |
| Tcadist | 1.525 | 1.532 | 1.525 | 1.53 |
| Icdist | 3.472 | 3.069 | 3.618 | 3.647 |
| Iodist | 3.677 | 3.072 | 3.286 | 3.657 |
| Indist | 4.507 | 4.556 | 4.708 | 4.178 |
| Itdist | 3.472 | 3.069 | 3.618 | 3.647 |
| Inum | 1644 | 1696 | 2089 | 1535 |
| Iname | CD2 | OD1 | CD1 | CB |
| Ichain | A | A | A | A |
| Iaaind | 206 | 213 | 258 | 190 |
| Iaanum | 252 | 259 | 279 | 209 |
| Iaaname | LEU | ASP | TYR | LEU |
| Iaass | H | E | H | C |
| Iaaphi | −94.9 | −110.9 | −69.5 | −73.2 |
| Iaapsi | −34.2 | 127.4 | −18.6 | −32.6 |
| Iomg | −173.5 | −178.2 | −177.8 | −177.1 |
| Ic1 | −63.9 | −171.8 | −79.4 | 167.9 |
| Ic2 | 167.9 | 57.6 | −57.1 | 69.8 |
| Ic3 | 999.9 | 999.9 | 999.9 | 999.9 |
| Ic4 | 999.9 | 999.9 | 999.9 | 999.9 |
| IUpAA | ASP | CYS | ILE | VAL |
| IDnAA | PHE | LEU | THR | PHE |
| Ibval | 6.09 | 32.79 | 37.22 | 8.29 |
| Iasa | 0.13 | 0 | 0 | 0 |
| K1cdist | 4.988 | 4.114 | 4.099 | 4.209 |
| K1odist | 5.113 | 3.819 | 3.526 | 4.6 |
| K1ndist | 5.733 | 5.402 | 5.704 | 4.874 |
| K1tdist | 4.988 | 4.114 | 4.099 | 4.209 |
| K1num | 1642 | 1695 | 2088 | 1532 |
| K1name | CG | CG | CG | CA |
| K1aanum | 252 | 259 | 279 | 209 |
| K1aaname | LEU | ASP | TYR | LEU |
| K2cdist | NoValue | NoValue | 3.857 | NoValue |
| K2odist | NoValue | NoValue | 3.951 | NoValue |
| K2ndist | NoValue | NoValue | 4.353 | NoValue |
| K2tdist | NoValue | NoValue | 3.857 | NoValue |
| K2num | NoValue | NoValue | 2091 | NoValue |
| K2name | NoValue | NoValue | CE1 | NoValue |
| K2aanum | NoValue | NoValue | 279 | NoValue |
| K2aaname | NoValue | NoValue | TYR | NoValue |
| Cx | 0 | 0 | 0 | 0 |
| Cy | 0 | 0 | 0 | 0 |
| Cz | 0 | 0 | 0 | 0 |
| CsphR | 0 | 0 | 0 | 0 |
| CsphT | 0 | 0 | 0 | 0 |
| CsphP | −3.142 | 0 | 3.142 | 0 |
| CcylR | 0 | 0 | 0 | 0 |
| CcylT | −3.142 | 0 | 3.142 | 0 |
| CcylZ | 0 | 0 | 0 | 0 |
| Ox | −0.628 | −0.629 | −0.659 | −0.666 |
| Oy | 0.998 | 1.004 | −0.754 | 1.028 |
| Oz | 0.364 | 0.341 | −0.689 | 0.182 |
| OsphR | 1.234 | 1.233 | 1.216 | 1.238 |
| OsphT | 1.271 | 1.291 | 2.173 | 1.423 |
| OsphP | 2.132 | 2.13 | −2.289 | 2.146 |
| OcylR | 1.234 | 1.233 | 1.216 | 1.238 |
| OcylT | 2.132 | 2.13 | −2.289 | 2.146 |
| OcylZ | 0.364 | 0.341 | −0.689 | 0.182 |
| Nx | 2.055 | 2.054 | 2.096 | 2.039 |
| Ny | 1.357 | 1.356 | 1.328 | 1.368 |
| Nz | 0 | 0 | 0 | 0 |
| NsphR | 2.463 | 2.461 | 2.481 | 2.455 |
| NsphT | 1.571 | 1.571 | 1.571 | 1.571 |

TABLE 2-continued

| | | | | |
|---|---|---|---|---|
| NsphP | 0.584 | 0.583 | 0.565 | 0.591 |
| NcylR | 2.463 | 2.461 | 2.481 | 2.455 |
| NcylT | 0.584 | 0.583 | 0.565 | 0.591 |
| NcylZ | 0 | 0 | 0 | 0 |
| Cax | 1.525 | 1.532 | 1.525 | 1.53 |
| Cay | 0 | 0 | 0 | 0 |
| Caz | 0 | 0 | 0 | 0 |
| CasphR | 1.525 | 1.532 | 1.525 | 1.53 |
| CasphT | 1.571 | 1.571 | 1.571 | 1.571 |
| CasphP | 0 | 0 | 0 | 0 |
| CacylR | 1.525 | 1.532 | 1.525 | 1.53 |
| CacylT | 0 | 0 | 0 | 0 |
| CacylZ | 0 | 0 | 0 | 0 |
| Tx | −12.209 | 3.16 | 17.53 | 11.229 |
| Ty | −17.125 | −7.179 | −33.077 | −23.148 |
| Tz | −3.618 | −14.31 | 38.22 | 26.483 |
| TsphR | | | | |
| TsphT | | | | |
| TsphP | | | | |
| TcylR | | | | |
| TcylT | | | | |
| TcylZ | | | | |
| Ix | −0.948 | −0.804 | −1.669 | −0.297 |
| Iy | 0.629 | −0.729 | 1.536 | 1.127 |
| Iz | −3.281 | 2.871 | −2.818 | −3.455 |
| IsphR | 3.473 | 3.069 | 3.617 | 3.646 |
| IsphT | 2.808 | 0.361 | 2.464 | 2.816 |
| IsphP | 2.556 | −2.405 | 2.398 | 1.828 |
| IcylR | 3.473 | 3.069 | 3.617 | 3.646 |
| IcylT | 2.556 | −2.405 | 2.398 | 1.828 |
| IcylZ | −3.281 | 2.871 | −2.818 | −3.455 |
| K1x | −1.194 | −1.35 | −2.979 | 0.085 |
| K1y | 1.1 | −0.243 | 1.098 | −0.13 |
| K1z | −4.717 | 3.878 | −2.593 | −4.206 |
| K1sphR | 4.989 | 4.113 | 4.099 | 4.209 |
| K1sphT | 2.81 | 0.34 | 2.256 | 3.105 |
| K1sphP | 2.397 | −2.963 | 2.788 | −0.992 |
| K1cylR | 4.989 | 4.113 | 4.099 | 4.209 |
| K1cylT | 2.397 | −2.963 | 2.788 | −0.992 |
| K1cylZ | −4.717 | 3.878 | −2.593 | −4.206 |
| K2x | NoValue | NoValue | −1.258 | NoValue |
| K2y | NoValue | NoValue | 2.771 | NoValue |
| K2z | NoValue | NoValue | −2.37 | NoValue |
| K2sphR | | | 3.857 | |
| K2sphT | | | 2.232 | |
| K2sphP | | | 1.997 | |
| K2cylR | | | 3.857 | |
| K2cylT | | | 1.997 | |
| K2cylZ | | | −2.37 | |
| inter | MS | MS | MS | MS |
| Icount | 1 | 6 | 4 | 4 |
| Tcount | 1 | 1 | 1 | 2 |

| id | out01:0000283 | out01:0000527 | out01:0000542 |
|---|---|---|---|
| pdbcode | 1a0pA | 1a12A | 1a12A |
| res | 2.5 | 1.7 | 1.7 |
| rval | 0.287 | 0.219 | 0.219 |
| org | *Escherichia coli* | *Homo sapiens* | *Homo sapiens* |
| Ichain | A | A | A |
| Taaind | 137 | 257 | 12 |
| Taanum | 156 | 277 | 32 |
| Taaname | THR | THR | THR |
| Taass | E | C | C |
| Taaphi | −105.2 | −114.7 | −127.1 |
| Taapsi | 174 | 1 | −10.7 |
| Tomg | 177.6 | −178.5 | −171.7 |
| Tc1 | 64.4 | 49.2 | 59.2 |
| Tc2 | 999.9 | 999.9 | 999.9 |
| Tc3 | 999.9 | 999.9 | 999.9 |
| Tc4 | 999.9 | 999.9 | 999.9 |
| TUpAA | LEU | GLY | SER |
| TDnAA | MET | GLU | GLU |
| Tnum | 1111 | 1919 | 93 |
| Tname | C | C | C |
| Tbval | 38.02 | 20.11 | 12.34 |
| Tasa | 0 | 0 | 0.21 |
| Tcdist | 0 | 0 | 0 |
| Todist | 1.239 | 1.247 | 1.249 |

TABLE 2-continued

| | | | |
|---|---|---|---|
| Tndist | 2.455 | 2.492 | 2.502 |
| Tcadist | 1.53 | 1.516 | 1.521 |
| Icdist | 3.199 | 3.432 | 3.67 |
| Iodist | 4.381 | 3.207 | 3.652 |
| Indist | 4.537 | 4.235 | 4.639 |
| Itdist | 3.199 | 3.432 | 3.67 |
| Inum | 1519 | 1845 | 372 |
| Iname | O | O | CG1 |
| Ichain | A | A | A |
| Iaaind | 188 | 247 | 50 |
| Iaanum | 207 | 267 | 70 |
| Iaaname | ASP | SER | VAL |
| Iaass | C | C | E |
| Iaaphi | −83.2 | −149.7 | −101.1 |
| Iaapsi | −14.4 | 38.2 | −21 |
| Iomg | −179.8 | −179.1 | 179.5 |
| Ic1 | 66 | −164 | −65.2 |
| Ic2 | −21.2 | 999.9 | 999.9 |
| Ic3 | 999.9 | 999.9 | 999.9 |
| Ic4 | 999.9 | 999.9 | 999.9 |
| IUpAA | ILE | LEU | VAL |
| IDnAA | VAL | ASN | GLN |
| Ibval | 43.39 | 9.22 | 8.96 |
| Iasa | 0 | 0 | 1.04 |
| K1cdist | 4.342 | 3.962 | 4.187 |
| K1odist | 5.553 | 3.395 | 4.575 |
| K1ndist | 5.334 | 5.257 | 4.346 |
| K1tdist | 4.342 | 3.962 | 4.187 |
| K1num | 1518 | 1844 | 371 |
| K1name | C | C | CB |
| K1aanum | 207 | 267 | 70 |
| K1aaname | ASP | SER | VAL |
| K2cdist | NoValue | NoValue | NoValue |
| K2odist | NoValue | NoValue | NoValue |
| K2ndist | NoValue | NoValue | NoValue |
| K2tdist | NoValue | NoValue | NoValue |
| K2num | NoValue | NoValue | NoValue |
| K2name | NoValue | NoValue | NoValue |
| K2aanum | NoValue | NoValue | NoValue |
| K2aaname | NoValue | NoValue | NoValue |
| Cx | 0 | 0 | 0 |
| Cy | 0 | 0 | 0 |
| Cz | 0 | 0 | 0 |
| CsphR | 0 | 0 | 0 |
| CsphT | 0 | 0 | 0 |
| CsphP | 0 | 0 | 0 |
| CcylR | 0 | 0 | 0 |
| CcylT | 0 | 0 | 0 |
| CcylZ | 0 | 0 | 0 |
| Ox | −0.666 | −0.609 | −0.582 |
| Oy | 1.028 | −1.084 | −1.095 |
| Oz | 0.182 | 0.085 | −0.146 |
| OsphR | 1.238 | 1.246 | 1.249 |
| OsphT | 1.423 | 1.503 | 1.688 |
| OsphP | 2.146 | −2.083 | −2.059 |
| OcylR | 1.238 | 1.246 | 1.249 |
| OcylT | 2.146 | −2.083 | −2.059 |
| OcylZ | 0.182 | 0.085 | −0.146 |
| Nx | 2.039 | 2.11 | 2.128 |
| Ny | 1.368 | 1.327 | 1.316 |
| Nz | 0 | 0 | 0 |
| NsphR | 2.455 | 2.493 | 2.502 |
| NsphT | 1.571 | 1.571 | 1.571 |
| NsphP | 0.591 | 0.561 | 0.554 |
| NcylR | 2.455 | 2.493 | 2.502 |
| NcylT | 0.591 | 0.561 | 0.554 |
| NcylZ | 0 | 0 | 0 |
| Cax | 1.53 | 1.516 | 1.521 |
| Cay | 0 | 0 | 0 |
| Caz | 0 | 0 | 0 |
| CasphR | 1.53 | 1.516 | 1.521 |
| CasphT | 1.571 | 1.571 | 1.571 |
| CasphP | 0 | 0 | 0 |
| CacylR | 1.53 | 1.516 | 1.521 |
| CacylT | 0 | 0 | 0 |
| CacylZ | 0 | 0 | 0 |

TABLE 2-continued

| | | | |
|---|---|---|---|
| Tx | 11.229 | 39.484 | 5.281 |
| Ty | −23.148 | −28.232 | −11.189 |
| Tz | 26.483 | 0.224 | 9.116 |
| TsphR | | | |
| TsphT | | | |
| TsphP | | | |
| TcylR | | | |
| TcylT | | | |
| TcylZ | | | |
| Ix | 0.852 | 1.533 | −0.362 |
| Iy | −2.85 | −2.417 | −0.092 |
| Iz | −1.176 | −1.893 | −3.651 |
| IsphR | 3.199 | 3.432 | 3.67 |
| IsphT | 1.947 | 2.155 | 3.04 |
| IsphP | −1.28 | −1.006 | −2.893 |
| IcylR | 3.199 | 3.432 | 3.67 |
| IcylT | −1.28 | −1.006 | −2.893 |
| IcylZ | −1.176 | −1.893 | −3.651 |
| K1x | 1.65 | 0.644 | 0.446 |
| K1y | −3.76 | −3.182 | 1.142 |
| K1z | −1.413 | −2.271 | −4.003 |
| K1sphR | 4.342 | 3.962 | 4.187 |
| K1sphT | 1.902 | 2.181 | 2.844 |
| K1sphP | −1.157 | −1.371 | 1.198 |
| K1cylR | 4.342 | 3.962 | 4.187 |
| K1cylT | −1.157 | −1.371 | 1.198 |
| K1cylZ | −1.413 | −2.271 | −4.003 |
| K2x | NoValue | NoValue | NoValue |
| K2y | NoValue | NoValue | NoValue |
| K2z | NoValue | NoValue | NoValue |
| K2sphR | | | |
| K2sphT | | | |
| K2sphP | | | |
| K2cylR | | | |
| K2cylT | | | |
| K2cylZ | | | |
| inter | MM | MM | MS |
| Icount | 4 | 4 | 2 |
| Tcount | 2 | 1 | 1 |

Key

| Header | Description |
|---|---|
| Id | Incremented Identifier of a contact. Every unique identifier is a unique theta-iota interaction. The id is eight digits with place-holding 0s (ex. 1 is 00000001). |
| pdbcode | The PDB code that was given in the input file. (ex 1mu4B for chain B of 1mu4, or 1mu4 for the structure). |
| res | The resolution of the PDB structure. |
| rval | The R-value of the PDB structure. |
| org | The organism source for the PDB structure. |
| Tchain | The chain identifier for the theta atom. |
| Taaind | The amino acid index for the theta amino acid (index starts at 1 for the first amino acid in the structure and increments for each amino acid) |
| Taanum | The amino acid number for the theta atom. |
| Taaname | The amino acid name for the theta atom. |
| Taass | The amino acid secondary structure for the theta atom. |
| Taaphi | The amino acid phi angle for the theta atom. |
| Taapsi | The amino acid psi angle for the theta atom. |
| Tomg | The amino acid omega angle for the theta atom. |
| Tchi1 | The amino acid chi 1 angle for the theta atom. |
| Tchi2 | The amino acid chi 2 angle for the theta atom. |
| Tchi3 | The amino acid chi 3 angle for the theta atom. |
| Tchi4 | The amino acid chi 4 angle for the theta atom. |
| TUpAA | The amino acid which is upstream of the theta amino acid. |
| TDnAA | The amino acid which is downstream of the theta amino acid. |
| Tnum | The atom number for the theta atom. |
| Tname | The atom name for the theta atom. |
| Tbval | The B value or temperature factor for the theta atom. |
| Tasa | The Accessible Surface Area of the theta atom. |
| Tcdist | The distance from the theta atom to the backbone Carbon. |

TABLE 2-continued

| | |
|---|---|
| Todist | The distance from the theta atom to the backbone Oxygen. |
| Tndist | The distance from the theta atom to the backbone Nitrogen. |
| Tcadist | The distance from the theta atom to the backbone Alpha Carbon. |
| Icdist | The distance from the iota atom to the backbone Carbon of the theta amino acid. |
| Iodist | The distance from the iota atom to the backbone Oxygen of the theta amino acid. |
| Indist | The distance from the iota atom to the backbone Nitrogen of the theta amino acid. |
| Itdist | The distance from the iota atom to the theta atom. |
| Inum | The atom number for the iota atom. |
| Iname | The atom name for the iota atom. |
| Ichain | The chain identifier for the iota atom. |
| Iaaind | The amino acid index for the iota amino acid (index starts at 1 for the first amino acid in the structure and increments for each amino acid) |
| Iaanum | The amino acid number for the iota atom. |
| Iaaname | The amino acid name for the iota atom. |
| Iaass | The amino acid secondary structure for the iota atom. |
| Iaaphi | The amino acid phi angle for the iota atom. |
| Iaapsi | The amino acid psi angle for the iota atom. |
| Iomg | The amino acid omega angle for the iota atom. |
| Ichil | The amino acid chi 1 angle for the iota atom. |
| Ichi2 | The amino acid chi 2 angle for the iota atom. |
| Ichi3 | The amino acid chi 3 angle for the iota atom. |
| Ichi4 | The amino acid chi 4 angle for the iota atom. |
| IUpAA | The amino acid which is upstream of the iota amino acid. |
| IDnAA | The amino acid which is downstream of the iota amino acid. |
| Ibval | The B value or temperature factor for the iota atom. |
| Iasa | The Accessible Surface Area for the iota atom. |
| Klcdist | The distance from the first kappa atom to the backbone Carbon of the theta amino acid. |
| Klodist | The distance from the first kappa atom to the backbone Oxygen of the theta amino acid. |
| Kindist | The distance from the first kappa atom to the backbone Nitrogen of the theta amino acid. |
| Kltdist | The distance from the first kappa atom to the theta atom. |
| Klnum | The atom number for the first kappa atom. |
| Klname | The atom name for the first kappa atom. |
| Klaanum | The amino acid number for the first kappa atom. |
| KIaaname | The amino acid name for the first kappa atom. |
| K2cdist | The distance from the second kappa atom to the backbone Carbon of the theta amino acid. |
| K2odist | The distance from the second kappa atom to the backbone Oxygen of the theta amino acid. |
| K2ndist | The distance from the second kappa atom to the backbone Nitrogen of the theta amino acid. |
| K2tdist | The distance from the second kappa atom to the theta atom. |
| K2num | The atom number for the second kappa atom. |
| K2name | The atom name for the second kappa atom. |
| K2aanum | The amino acid number for the second kappa atom. |
| K2aaname | The amino acid name for the second kappa atom. |
| Cx | The Theta-superimposed x coordinate for the backbone Carbon atom of the theta AA. |
| Cy | The Theta-superimposed y coordinate for the backbone Carbon atom of the theta AA. |
| Cz | The Theta-superimposed z coordinate for the backbone Carbon atom of the theta AA. |
| CsphR | The Theta-superimposed spherical polar distance for the backbone Carbon of the theta AA. |
| CsphT | The Theta-superimposed spherical polar latitude angle for the backbone Carbon of the theta AA. |
| CsphP | The Theta-superimposed spherical polar longitude angle for the backbone Carbon of the theta AA. |
| CcylR | The Theta-superimposed cylindrical polar distance for the backbone Carbon of the theta AA. |
| CcylT | The Theta-superimposed cylindrical polar angle for the backbone Carbon of the theta AA. |
| CcylZ | The Theta-superimposed cylindrical polar z coordinate for the backbone Carbon of the theta AA. |
| Ox | The Theta-superimposed x coordinate for the backbone Oxygen atom of the theta AA. |

TABLE 2-continued

| | |
|---|---|
| Oy | The Theta-superimposed y coordinate for the backbone Oxygen atom of the theta AA. |
| Oz | The Theta-superimposed z coordinate for the backbone Oxygen atom of the theta AA. |
| OsphR | The Theta-superimposed spherical polar distance for the backbone Oxygen of the theta AA. |
| OsphT | The Theta-superimposed spherical polar latitude angle for the backbone Oxygen of the theta AA. |
| OsphP | The Theta-superimposed spherical polar longitude angle for the backbone Oxygen of the theta AA. |
| OcylR | The Theta-superimposed cylindrical polar distance for the backbone Oxygen of the theta AA. |
| OcylT | The Theta-superimposed cylindrical polar angle for the backbone Oxygen of the theta AA. |
| OcylZ | The Theta-superimposed cylindrical polar z coordinate for the backbone Oxygen of the theta AA. |
| Nx | The Theta-superimposed x coordinate for the backbone Nitrogen atom of the theta AA. |
| Ny | The Theta-superimposed y coordinate for the backbone Nitrogen atom of the theta AA. |
| Nz | The Theta-superimposed z coordinate for the backbone Nitrogen atom of the theta AA. |
| NsphR | The Theta-superimposed spherical polar distance for the backbone Nitrogen of the theta AA. |
| NsphT | The Theta-superimposed spherical polar latitude angle for the backbone Nitrogen of the theta AA. |
| NsphP | The Theta-superimposed spherical polar longitude angle for the backbone Nitrogen of the theta AA. |
| NcylR | The Theta-superimposed cylindrical polar distance for the backbone Nitrogen of the theta AA. |
| NcylT | The Theta-superimposed cylindrical polar angle for the backbone Nitrogen of the theta AA. |
| NcylZ | The Theta-superimposed cylindrical polar z coordinate for the backbone Nitrogen of the theta AA. |
| Cax | The Theta-superimposed x coordinate for the Alpha Carbon atom of the theta AA. |
| Cay | The Theta-superimposed y coordinate for the Alpha Carbon atom of the theta AA. |
| Caz | The Theta-superimposed z coordinate for the Alpha Carbon atom of the theta AA. |
| CasphR | The Theta-superimposed spherical polar distance for the Alpha Carbon of the theta AA. |
| CasphT | The Theta-superimposed spherical polar latitude angle for the Alpha Carbon of the theta AA. |
| CasphP | The Theta-superimposed spherical polar longitude angle for the Alpha Carbon of the theta AA. |
| CacylR | The Theta-superimposed cylindrical polar distance for the Alpha Carbon of the theta AA. |
| CacylT | The Theta-superimposed cylindrical polar angle for the Alpha Carbon of the theta AA. |
| CacylZ | The Theta-superimposed cylindrical polar z coordinate for the Alpha Carbon of the theta AA. |
| Tx | The Theta-superimposed x coordinate for the theta atom. |
| Ty | The Theta-superimposed y coordinate for the theta atom. |
| Tz | The Theta-superimposed z coordinate for the theta atom. |
| TsphR | The Theta-superimposed spherical polar distance for the Theta atom. |
| TsphT | The Theta-superimposed spherical polar latitude angle for the Theta atom. |
| TsphP | The Theta-superimposed spherical polar longitude angle for the Theta atom. |
| TcylR | The Theta-superimposed cylindrical polar distance for the Theta atom. |
| TcylT | The Theta-superimposed cylindrical polar angle for the Theta atom. |
| TcylZ | The Theta-superimposed cylindrical polar z coordinate for the Theta atom. |
| Ix | The Theta-superimposed x coordinate for the iota atom. |
| Iy | The Theta-superimposed y coordinate for the iota atom. |
| Iz | The Theta-superimposed z coordinate for the iota atom. |
| IsphR | The Theta-superimposed spherical polar distance for the iota atom. |
| IsphT | The Theta-superimposed spherical polar latitude angle for the iota atom. |

TABLE 2-continued

| | |
|---|---|
| IsphP | The Theta-superimposed spherical polar longitude angle for the iota atom. |
| IcylR | The Theta-superimposed cylindrical polar distance for the iota atom. |
| IcylT | The Theta-superimposed cylindrical polar angle for the iota atom. |
| IcylZ | The Theta-superimposed cylindrical polar z coordinate for the iota atom. |
| K1x | The Theta-superimposed x coordinate for the first kappa atom. |
| K1y | The Theta-superimposed y coordinate for the first kappa atom. |
| K1z | The Theta-superimposed z coordinate for the first kappa atom. |
| K1sphR | The Theta-superimposed spherical polar distance for the first kappa atom. |
| K1sphT | The Theta-superimposed spherical polar latitude angle for the first kappa atom. |
| K1sphP | The Theta-superimposed spherical polar longitude angle for the first kappa atom. |
| K1cylR | The Theta-superimposed cylindrical polar distance for the first kappa atom. |
| K1cylT | The Theta-superimposed cylindrical polar angle for the first kappa atom. |
| K1cylZ | The Theta-superimposed cylindrical polar z coordinate for the first kappa atom. |
| K2x | The Theta-superimposed x coordinate for the second kappa atom. |
| K2y | The Theta-superimposed y coordinate for the second kappa atom. |
| K2z | The Theta-superimposed z coordinate for the second kappa atom. |
| K2sphR | The Theta-superimposed spherical polar distance for the second kappa atom. |
| K2sphT | The Theta-superimposed spherical polar latitude angle for the second kappa atom. |
| K2sphP | The Theta-superimposed spherical polar longitude angle for the second kappa atom. |
| K2cylR | The Theta-superimposed cylindrical polar distance for the second kappa atom. |
| K2cylT | The Theta-superimposed cylindrical polar angle for the second kappa atom. |
| K2cylZ | The Theta-superimposed cylindrical polar z coordinate for the second kappa atom. |
| inter | The type of interaction for the theta & iota contact: MM-Main chain to Main chain, MS-Main chain to Side chain, SM . . . , SS . . . where the first letter refers to theta and the second refers to iota. |
| Icount | The iota atom count for the particular theta atom. |
| Tcount | The theta atom count for the particular amino acid. |

Visualisation of IL17F Iota Datasets

Each iota dataset was visualized in relation to the IL17F/Fab 496 structure using molecular graphics computer software such as Pymol. This could be done by direct plotting of the iota dataset as individual points or by first mathematically transforming the dataset into a density function and a file format compatible for molecular graphic display e.g. ccp4, so that contour maps of higher density could be displayed over the IL17 epitope.

Inspection of Iota Density Mapsfor Intersection with Fab 496 Paratope Atoms

The IL17F/Fab 496 interface was examined to determine the degree of intersection between individual Fab 496 atoms per residue and the corresponding iota density maps. Residues were identified where there was no or little intersection. In these cases alternative residues were substituted via the molecular graphics software to determine whether better intersection could be achieved between residue atoms and relevant iota density maps. Amino acid substitutions producing good iota density map intersection were short listed for in vitro production and testing as single point mutations as intact IgG versions of Fab 496.

DNA manipulations and General Methods

*E. coli* strain INVaF (Invitrogen) was used for transformation and routine culture growth. DNA restriction and modification enzymes were obtained from Roche Diagnostics Ltd. and New England Bio labs. Plasmid preparations were performed using Maxi Plasmid™ purification kits (Qiagen, catalogue No. 12165). DNA sequencing reactions were performed using ABI Prism Big Dye™ terminator sequencing kit (catalogue No. 4304149) and run on an ABI 3100 automated sequencer (Applied Biosystems). Data was analysed using the program Auto Assembler (Applied Biosystems). Oligonucleotides were obtained from Invitrogen. The concentration of IgG was determined by IgG assembly ELISA.

Affinity Maturation of Antibody CA028_00496

CA028_0496 is a humanised neutralising antibody which binds both IL17A and IL17F isoforms. It comprises the grafted variable regions, termed gL7 and gH9, whose sequences are disclosed in WO 2008/047134. The wild type Fab' fragment of this antibody (Fab 496) and mutant variants were prepared as follows: oligonucleotide primer sequences were designed and constructed in order to introduce single point mutations in the light chain variable region (gL7) as per residues and positions determined in the above short list. Each mutated light chain was separately sub-cloned into the UCB Celltech human light chain expression vector pKHlO.1, which contained DNA encoding the human C-kappa constant region (Km3 allotype). The unaltered heavy chain variable region (gH9) sequence was sub-cloned into the UCB Celltech expression vector pVhglFab6His which contained DNA encoding human heavy chain gamma-1 constant region, CHI. Heavy and light chain encoding plasmids were co-transfected into HEK293 cells using the 293fectinTM procedure according to the manufacturer's instructions (InVitrogen. Catalogue No. 12347-019). IgG1 antibody levels secreted into the culture supematants after 10 to 12 days culture were assessed by ELISA and binding kinetics assessed by surface plasmon resonance (see below). Mutants showing improved or similar binding to IL17F were then prepared and tested in combination as double, triple, quadruple or quintuple light chain mutations as above.

Surface Plasmon Resonance (SPR)

All SPR experiments were carried out on a Biacore 3000 system (Biacore AB) at 25° C. using HBS-EP running buffer (10 mM HEPES pH 7.4, 150 mM NaCl 3 mM EDTA 0.005% (v/v) surfactant P20, Biacore AB). Goat $F(ab')_2$ anti-IgG Fab'specific antibody (Jackson Labs. Product code 109-006-097) was covalently attached to the surface of a CM5 sensor chip (GE Healthcare) by the amine coupling method, as recommended by the manufacturers. Briefly, the carboxymethyl dextran surface was activated with a fresh mixture of 50 mM N-hydroxysuccimide and 200 mM 1-ethyl-3-(3-dimethylaminopropye-carbodiimide for 5 minutes at a flow rate of 10 μï/min Anti-Fab antibody at 50 μg/ml in 10 mM sodium acetate pH 5.0 buffer was injected for 60 sec at the same flow rate. Finally the surface was deactivated with a 10 minute pulse of 1 M ethanolamine.HCl pH8.5, leaving of 4000 to 5000 response units (RU) of immobilized antibody on the chip. A reference flow cell was prepared on the same chip by omitting the protein from the above procedure.

Wild type and mutated 496 Fabs were harvested from culture supematants in the range 3 to 30 μg/ml and crude supematants were diluted in running buffer into the range 0.5 to 2 μg/ml. In order to evaluate binding kinetics to IL17F, each antibody was first captured on the anti-Fab'surface by injection at 10 μï/ min for 60 sec to yield an additional 150 to 250 RU signal. Recombinant human IL17F was titrated from 10 nM in running buffer and injected at 30 μï/ml, to produce an association phase over 180 sec followed by a dissociation phase of 300 sec. At the end of each cycle the surface was regenerated with a 60 sec pulse of 40 mM HCl followed by a 30 sec pulse of 5 mM NaOH at 10 μï/min For each Fab' a control cycle was carried out where the IL17F injection was replaced with an injection of running buffer.

Sensograms were corrected by subtraction of reference flow cell signal, then by subtracting the control cycle sensogram for the respective Fab'. Dissociation rate constants (kd) and association rate constants ($k_a$) were fitted to the data using Biaevaluation software (Biacore AB). Fab affinities ($K_D$) were calculated as $K_D$=kd/$k_a$.

Results

Intersection of Iota Density Maps with Fab 496 Atoms

Inspection of that part of the surface of Fab 496 forming the interface with IL17F revealed that in many areas there was complete intersection between a given Fab 496 atom and the corresponding iota density map. This was particularly the case for amino acid residues comprising the Fab 496 heavy chain. However there were a number of regions comprising the light chain where there was no intersection or little intersection of Fab 496 atoms and corresponding iota density maps (Panel A, FIGS. 8 to 13).

Figure 8:
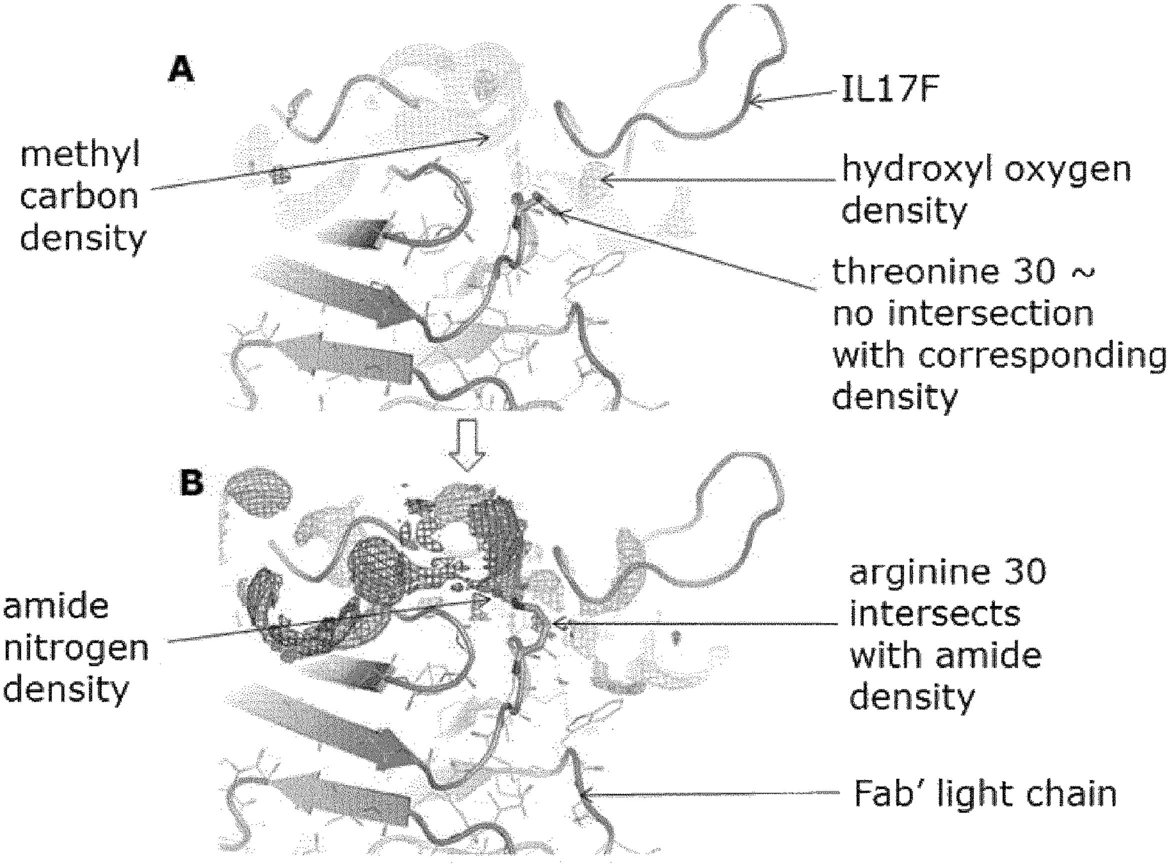
FIG. 8 is a computer generated visualization depicting a light chain threonine 30 to arginine 30 mutation.

By substituting alternative residues into the Fab 496 structure at these positions it was possible to achieve intersection between one or more atoms of the substituted residue and the corresponding iota density maps. (Panel B , FIGS. 8 to 13). Thus on Fab 496 light chain the threonine 30 Cy2 atom does not intersect with the methyl carbon iota density map and the Oyï atom does not intersect with the hydroxyl oxygen iota density map. However when threonine 30 is mutated to arginine, there is intersection between the NE atom and the secondary amide iota density map (FIG. 8).

Figure 9:
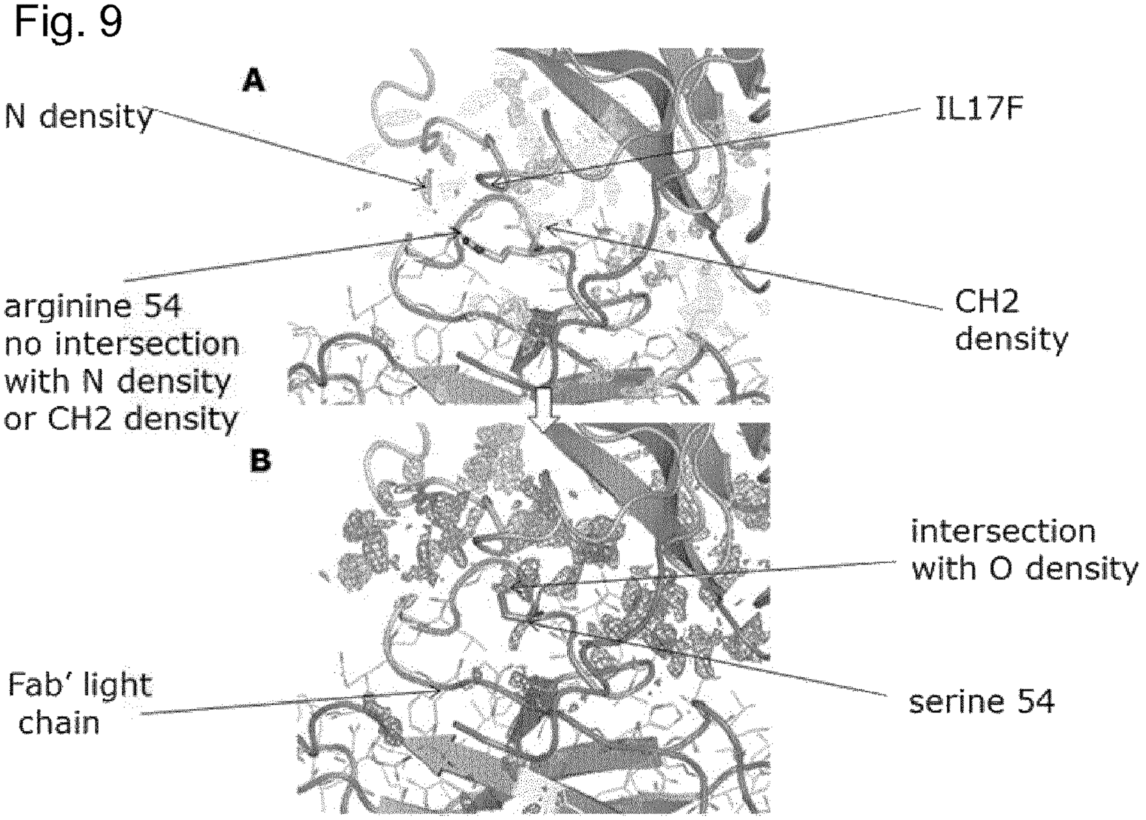
FIG. 9 is a computer generated visualization depicting a light chain arginine 54 to serine 54 mutation.
Figure 10:
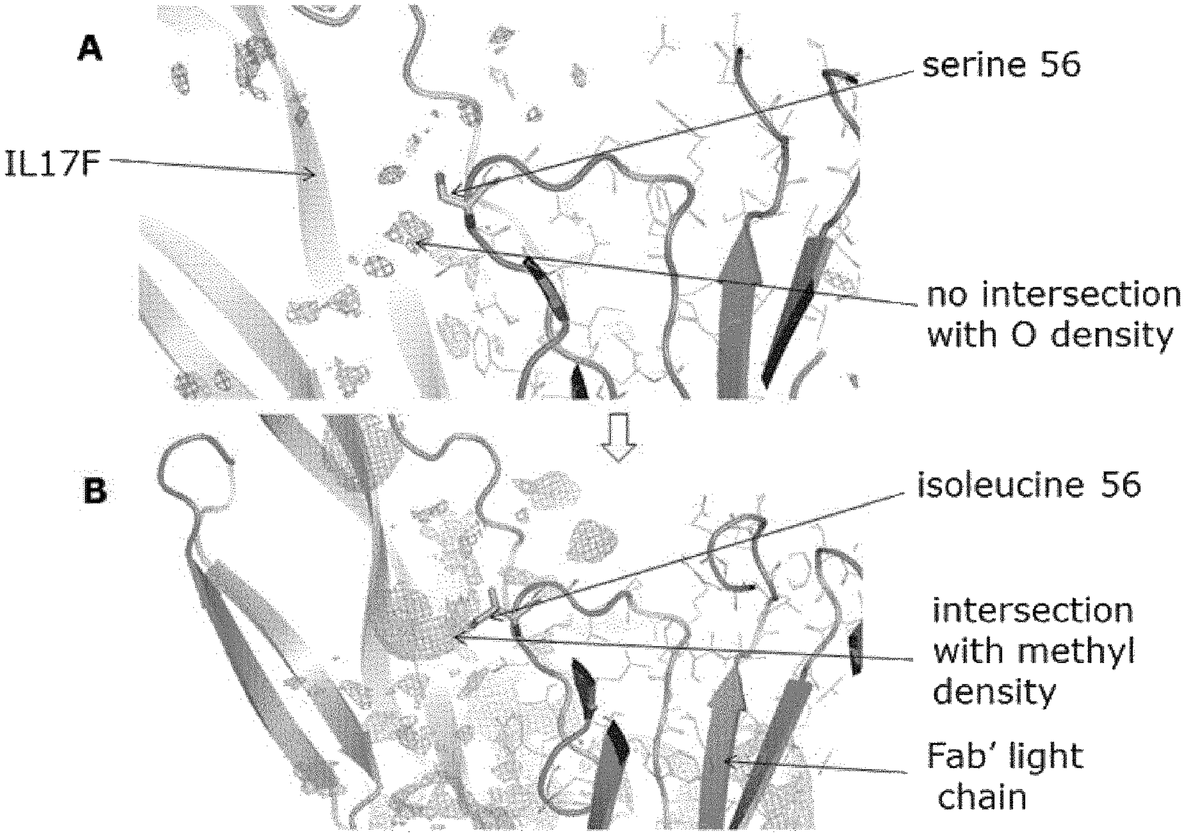
FIG. 10 is a computer generated visualization depicting a light chain serine 56 to isoleucine 56 mutation.
Figure 11:
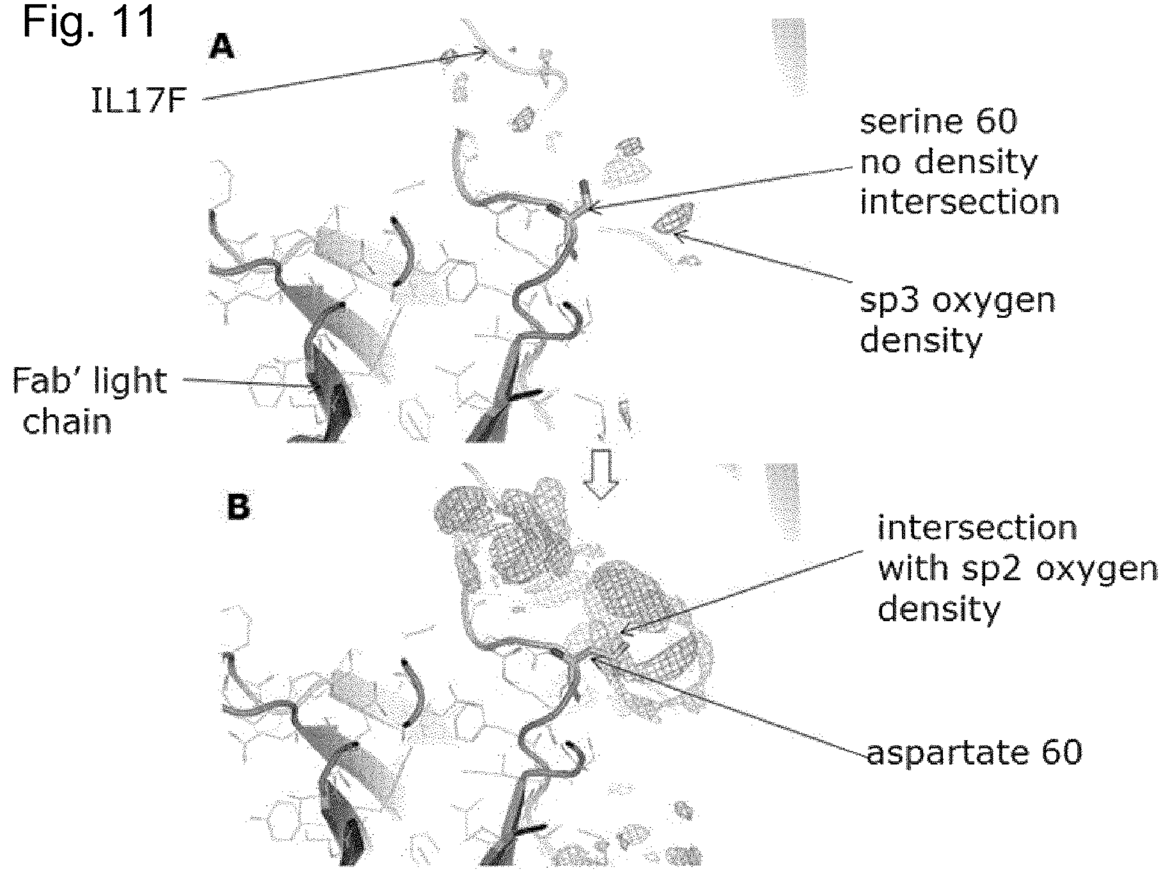
FIG. 11 is a computer generated visualization depicting a light chain serine 60 to aspartate 60 mutation.
Figure 12:
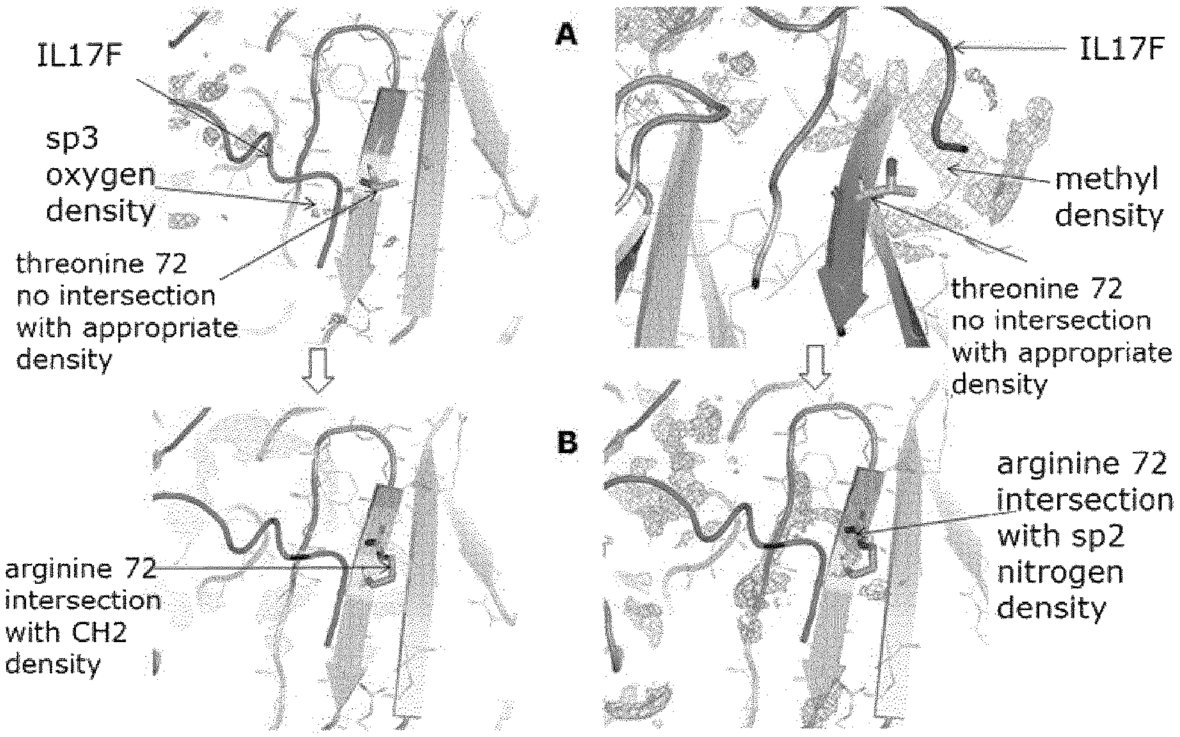
FIG. 12 is a computer generated visualization depicting a light chain threonine 72 to arginine 72 mutation.
Figure 13:
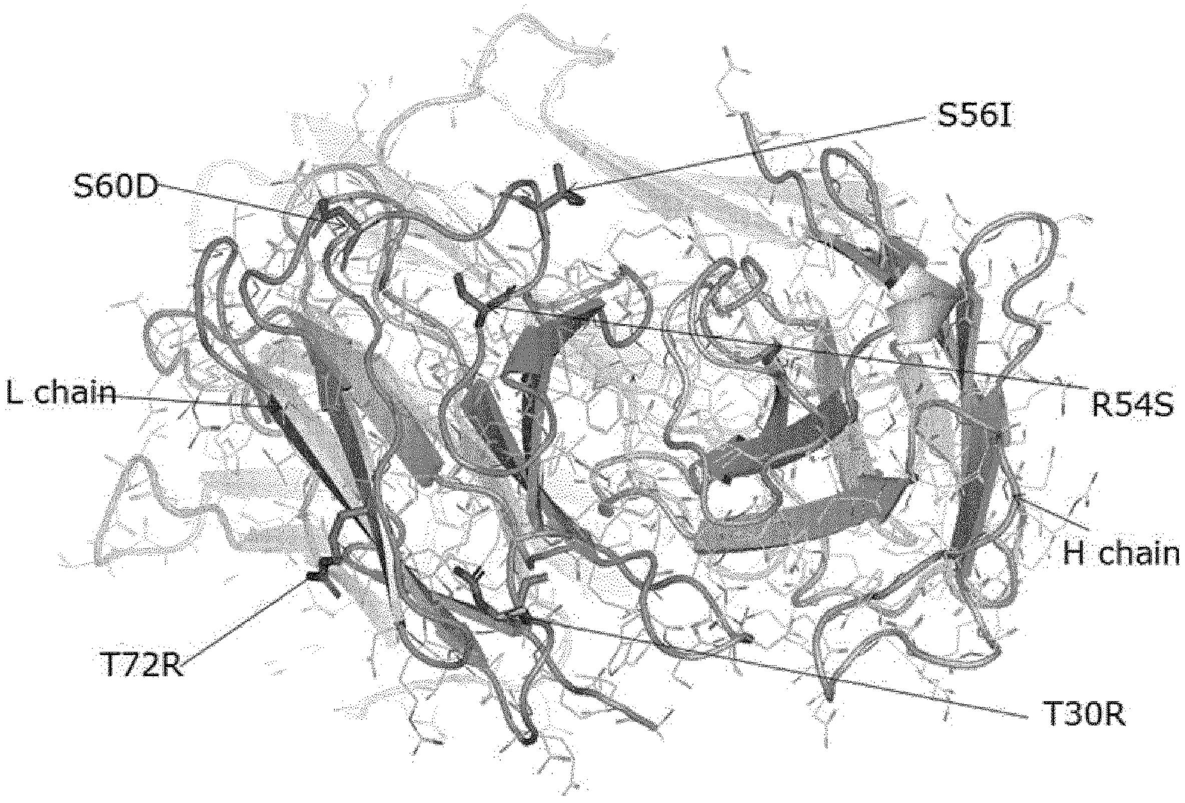
FIG. 13 is a computer generated visualization depicting the combination of 5 mutations in antibody 496i light chain resulting in a 180-fold improved affinity to IL17F.

FIG. 9 shows tetrahedral methylene iota density and secondary amide iota density dispersed around light chain arginine 54 without any intersection with respective side chain atoms of this residue. Conversely when mutated to a serine at this position there is good intersection of hydroxyl oxygen iota density and the gamma oxygen atom of the serine side chain. The light chain serine 56 gamma oxygen atom does not intersect with hydroxyl oxygen iota density. However when this residue is mutated to isoleucine there is intersection of the delta 1 methyl atom of the isoleucine side chain and methyl iota density (FIG. 10). In the case of serine 60, again the gamma oxygen is too distant from adjacent hydroxyl oxygen iota density to achieve intersection, (FIG. 11), but mutating this residue to aspartate brings about intersection of the side chain delta oxygen atom with carboxyl oxygen iota density.

Light chain threonine 72 is not a CDR residue but part of framework 3, its side chain methyl atom does not intersect with methyl carbon iota density nor its side chain oxygen atom with hydroxyl oxygen iota density. But the arginine 72 mutation allows intersection of both side chain delta carbon atom with methylene carbon iota density and of side chain eta nitrogen atoms with guanidinium nitrogen iota density.

Effects of Iota Designed Mutations on Antibody CA028_00496 on Binding Kinetics

Five iota designed single point light chain mutations in Fab 496, T30R, R54S, S56I, S60D and T72R, showed small improvements in binding affinity ranging from 1.7 to 3.6 fold. The improvement observed with the non-CDR mutation, T72R, was surprising since residues at this position do not normally contact the antigen. For all but one of these mutations (S60D), the improvement was driven by a reduction in dissociation rate constant (Table 3). Combinations of these mutations in pairs resulted in a synergistic improvement in binding, with a 3.8 to 7.5 fold reduction in dissociation rate constant; with triple and quadruple combinations producing further step reductions in dissociation rate constant (Table 3).

The combination of all five light chain mutations produced the largest improvement in binding affinity (Table 4) to give an affinity value of 11 pM to IL17F, some 180-fold better than the original Fab 496. An important finding was that there was no deleterious effect on the binding to the IL17A isoform, in fact an improvement, with affinity constant at 2 pM compared to 14 pM for the original Fab 496. It is interesting that combinations of the designed mutations produce a synergistic enhancement of affinity; one explanation is that they are reasonably spaced across the light chain paratope surface (FIG. 13) and therefore avoid negative interaction effects.

TABLE 3

Effect of single residue and combined residue light chain mutations of antibody CA028_000496 on IL17F dissociation rate constant

| CA028_00496 light chain mutations | $k_d$ ($s^{-1}$) | fold change |
|---|---|---|
| wt | 4.2E−03 | |
| T30R | 3.2E−03 | 1.3 |
| R54S | 2.1E−03 | 2.0 |
| S56I | 3.0E−03 | 1.4 |
| S60D | 4.1E−03 | 1.0 |
| T72R | 2.5E−03 | 1.7 |
| T30R/R54S | 7.0E−04 | 5.8 |
| T30R/S56I | 1.1E−03 | 3.8 |
| R54S/S56I | 6.2E−04 | 6.6 |
| R54S/T72R | 5.5E−04 | 7.5 |
| S56I/T72R | 8.0E−04 | 5.1 |
| S60D/T72R | 1.2E−03 | 3.6 |
| T30R/R54S/T72R | 2.5E−04 | 19 |
| T30R/S56I/T72R | 4.1E−04 | 10 |
| T30R/S56I/S60D/T72R | 3.1E−04 | 14 |
| T30R/R54S/S56I/T72R | 1.3E−04 | 35 |
| T30R/R54S/S60D/T72R | 9.3E−05 | 44 |
| T30R/R54S/S56I/S60D/T72R | 5.4E−05 | 104 |

TABLE 4

Affinity constant of antibody CA028_000496 versus variant comprising 5 light chain mutations

| | $k_a$ (MV) | kd ($s^{-1}$) | $K_D$ (M) | $K_D$ (pM) |
|---|---|---|---|---|
| wild type | 2.0E+06 | 4.1E−03 | 2.0E−09 | 2000 |
| T30R/R54S/S56I/ S60D/T72R | 2.3E+06 | 2.6E−05 | 1.1E−11 | 11 |

Conclusion

The method of creating iota density maps over the epitope surface of IL17F in order to predict favourable mutations in the corresponding antibody, Fab 496, has proven to be successful in that the affinity constant has been improved 180-fold to a $K_D$ of 11 pM. This method does not assume that only CDR mutations can be used but demonstrates that framework region mutations are also important for affinity maturation.

EXAMPLE 2

Utilisation of an Automated Process of the Invention in the Region Between an Ab's Heavy/Light Chains to Improve Stability Methods Identification of Target (Theta) Atoms of Both the Heavy and Light Chains of the Fv Interface of Fab X Using the coordinates of the crystal structure of an antibody Fab fragment "Fab X" complexed with antigen, all heavy chains atoms within 6 A of any light chain atoms were identified as epitope atoms (167 theta atoms listed in Table 5). Similarly, all light chains atoms within 6 A of any heavy chain atoms were identified as epitope atoms (159 theta atoms listed in Table 5).

TABLE 5

List of atoms comprising the heavy and light chain epitopes where the notation (1)-(2)-(3) designates (I) the respective H and L chains of Fab X, (2) residue number and (3) the atom type. Binding pocket (THETA) = H Binding partner (IOTA) = L

| | | | |
|---|---|---|---|
| H-47-CA | H-57-0 | H-104-OH | H-117-N |
| H-47-CB | H-60-CB | H-109-CB | H-117-0 |
| H-47-CG1 | H-60-CD1 | H-109-CG1 | H-117-0H |
| H-47-CG2 | H-60-CG1 | H-109-CG2 | H-118-C |
| H-49-CB | H-60-CG2 | H-112-CD1 | H-118-CA |
| H-49-CD | H-62-CE2 | H-112-CE1 | H-118-CB |
| H-49-CG | H-62-CH2 | H-112-CE2 | H-118-CD1 |
| H-49-NE2 | H-62-CZ2 | H-112-CZ | H-118-CD2 |
| H-49-OE1 | H-62-NE1 | H-112-OH | H-118-CE1 |
| H-53-C | H-68-C | H-113-C | H-118-CE2 |
| H-53-CA | H-68-CA | H-113-CA | H-118-CG |
| H-53-0 | H-68-CB | H-113-CB | H-118-CZ |
| H-54-C | H-68-CD1 | H-113-0 | H-118-N |
| H-54-CA | H-68-CD2 | H-113-OG | H-118-0 |
| H-54-N | H-68-CE1 | H-114-C | H-119-C |
| H-54-0 | H-68-CE2 | H-114-CA | H-119-CA |
| H-55-C | H-68-CG | H-114-CB | H-119-CB |
| H-55-CA | H-68-CZ | H-114-CG2 | H-119-CG |
| H-55-CB | H-68-N | H-114-N | H-119-N |
| H-55-CD1 | H-68-0 | H-114-0 | H-119-0 |
| H-55-CD2 | H-69-C | H-114-OG1 | H-121-C |
| H-55-CG | H-69-CA | H-115-C | H-121-CA |
| H-55-N | H-69-N | H-115-CA | H-121-CB |
| H-55-0 | H-69-0 | H-115-CB | H-121-CD1 |
| H-56-C | H-70-C | H-115-N | H-121-CD2 |
| H-56-CA | H-70-CA | H-115-0 | H-121-CE2 |
| H-56-CB | H-70-CB | H-116-C | H-121-CE3 |
| H-56-N | H-70-N | H-116-CA | H-121-CG |
| H-56-0 | H-70-O | H-116-CB | H-121-CH2 |
| H-57-C | H-71-C | H-116-CD | H-121-CZ2 |
| H-57-CA | H-71-CA | H-116-CG | H-121-CZ3 |
| H-57-CB | H-71-CB | H-116-N | H-121-N |
| H-57-CD1 | H-71-CG2 | H-116-0 | H-121-NE1 |
| H-57-CD2 | H-71-N | H-117-C | H-121-0 |
| H-57-CE2 | H-71-OG1 | H-117-CA | H-122-C |
| H-57-CE3 | H-72-N | H-117-CB | H-122-CA |
| H-57-CG | H-104-CD 1 | H-117-CD1 | H-122-N |
| H-57-CH2 | H-104-CD2 | H-117-CD2 | H-122-0 |
| H-57-CZ2 | H-104-CE1 | H-117-CE1 | H-123-C |
| H-57-CZ3 | H-104-CE2 | H-117-CE2 | H-123-CA |
| H-57-N | H-104-CG | H-117-CG | H-123-0 |
| H-57-NE1 | H-104-CZ | H-117-CZ | L-106-CG2 |
| L-11-OD1 | L-52-C | L-60-CZ | L-106-N |
| L-41-0 | L-52-0 | L-60-N | L-106-O |
| L-42-C | L-53-C | L-60-O | L-107-C |
| L-42-CA | L-53-CA | L-61-C | L-107-CA |
| L-42-CB | L-53-N | L-61-CA | L-107-CB |
| L-42-0 | L-53-0 | L-61-CB | L-107-N |
| L-43-C | L-54-C | L-61-CD | L-107-O |
| L-43-CA | L-54-CA | L-61-CG | L-107-OG |
| L-43-CB | L-54-CB | L-61-N | L-108-C |
| L-43-CD1 | L-54-N | L-61-0 | L-108-CA |
| L-43-CD2 | L-54-0 | L-61-OE1 | L-108-CB |
| L-43-CE1 | L-55-C | L-61-OE2 | L-108-CG |
| L-43-CE2 | L-55-CA | L-62-N | L-108-N |
| L-43-CG | L-55-CB | L-64-NZ | L-108-OD1 |
| L-43-CZ | L-55-CD | L-66-CG2 | L-108-OD2 |
| L-43-N | L-55-CG | L-98-CB | L-109-C |
| L-43-0 | L-55-N | L-98-CD1 | L-109-CA |
| L-44-C | L-55-0 | L-98-CD2 | L-109-CB |
| L-44-CA | L-56-C | L-98-CE1 | L-109-CG2 |
| L-44-N | L-56-CA | L-98-CE2 | L-109-N |
| L-44-0 | L-56-CB | L-98-CG | L-109-O |
| L-45-C | L-56-N | L-98-CZ | L-109-OG1 |
| L-45-CA | L-56-0 | L-98-OH | L-110-CA |
| L-45-CB | L-57-C | L-100-C | L-110-N |
| L-45-N | L-57-CA | L-100-CA | L-111-CA |
| L-45-0 | L-57-CB | L-100-N | L-111-CB |
| L-45-OG | L-57-CD1 | L-100-0 | L-111-CD1 |
| L-47-CB | L-57-CD2 | L-101-C | L-111-CD2 |
| L-47-CD1 | L-57-CG | L-101-CA | L-111-CE1 |
| L-47-CD2 | L-57-N | L-101-N | L-111-CE2 |
| L-47-CE1 | L-59-C | L-101-0 | L-111-CG |
| L-47-CE2 | L-59-0 | L-102-C | L-111-CZ |
| L-47-CG | L-60-C | L-102-CA | L-111-N |

TABLE 5-continued

List of atoms comprising the heavy and light chain epitopes where the notation (1)-(2)-(3) designates (I) the respective H and L chains of Fab X, (2) residue number and (3) the atom type.
Binding pocket (THETA) = H Binding partner (IOTA) = L

| | | | |
|---|---|---|---|
| L-47-CZ | L-60-CA | L-102-N | L-111-0 |
| L-47-OH | L-60-CB | L-105-O | L-112-0 |
| L-49-CB | L-60-CD1 | L-106-C | L-113-C |
| L-49-CD | L-60-CD2 | L-106-CA | L-113-CA |
| L-49-CG | L-60-CE1 | L-106-CB | L-113-0 |
| L-49-NE2 | L-60-CE2 | L-106-CD1 | |
| L-49-OE1 | L-60-CG | L-106-CG1 | |

Superimposition of Iota Data Over the Heavy and Light Chain Interface Surface

For each of the 167 theta atoms comprising the heavy chain epitope, the corresponding theta contact set was selected from the IOTA database and from that, an appropriate iota sub-group was selected e.g. carbonyl oxygen. The relative iota coordinates from this sub-group were transposed relative to the reference frame of the given theta atom of the heavy chain epitope. An iota dataset for a given sub-group was thus accumulated over the whole heavy chain epitope. In cases where the location of a given iota data point intersected with an atom of the heavy chain, closer than the sum of their respective Van der Waals radii minus 0.2 Å, then these data points were excluded from the dataset. The process was repeated for all relevant iota sub-groups to produce a series of iota datasets for the heavy chain epitope.

For each of the 159 theta atoms comprising the light chain epitope, the corresponding theta contact set was selected from the IOTA database and from that, an appropriate iota sub-group was selected e.g. carbonyl oxygen. The relative iota coordinates from this sub-group were transposed relative to the reference frame of the given theta atom of the heavy chain epitope. An iota dataset for a given sub-group was thus accumulated over the whole light chain epitope. In cases where the location of a given iota data point intersected with an atom of the light chain, closer than the sum of their respective Van der Waals radii minus 0.2 Å, then these data points were excluded from the dataset. The process was repeated for all relevant iota sub-groups to produce a series of iota datasets for the light chain epitope.

Inspection of Iota Density Mapsfor Intersection with Heavy-Light Chain Atoms

The whole process was automatically performed with an internal customised Rosetta python library script tailored for mutable positions identification, single point mutant generation, low-energy rotamer state enumeration, quantitative IOTA score computation, VH-VL chains binding energy estimation, and point mutants prioritisation.

Two scoring methods were used for mutants ranking:

1. AIOTAScore

Aforementioned IOTA density maps generated were used to compute the spatial intersection values between each heavy atom of residue at each mutable position and the density critical points in the corresponding type of maps nearby. IOTAScore is the sum of the volumetric overlaps between the heavy atoms of one residue with the maximum of IOTA densities with the corresponding type definitions, which reflects the degree of intersection between individual Fab X atoms per residue and the corresponding iota density maps. IOTAScore is negative numerically, where lower values imply more intersection. AIOTAScore is the change of lOTAScores between the mutant residue and the wildtype one; similarly, the more negative the AIOTAScore value the greater the implication that the mutant is more favoured than the wildtype one.

2. Rosetta ΔΔG Score

The Rosetta energy function is a linear combination of terms that model interaction forces between atoms, solvation effects, and torsion energies. More specifically, Score 12, the default full atom energy function in Rosetta is composed of a Lennard-Jones term, an implicit solvation term, an orientation-dependent hydrogen bond term, sidechain and backbone torsion potentials derived from the PDB, a short-ranged knowledge-based electrostatic term, and reference energies for each of the 20 amino acids that model the unfolded state. The binding strength between two binding partners, or AG, can be computed by subtracting the Rosetta scores of the individual partners alone with that of the complex structure formed by the two partners. Lower AG implies stronger binding. ΔΔG is the change of AG between the mutant complex and the wildtype one; the more negative the ΔΔG value the greater the implication that the mutant binding affinity is higher than the wildtype one.

FIG. 14 illustrates the workflow for in silico predicting point mutation at the VH-VL interface of the Fab X structure.

In step S101, all residues on the heavy chain with at least one heavy atom within 8 A of any light chain heavy atoms were identified as mutable positions. Similarly, all the residues on light chain with at least one heavy atom within 8 A of any heavy chain heavy atoms were identified as mutable positions.

In step SI02, for the wildtype Fab X crystal structure, the residue-wise lOTAScores and binding energy AG are computed, respectively. In step SI02.1, the IOTAScore for the wildtype residue on the current mutable position with the corresponding IOTA density maps nearby is computed, termed as (IOTAScorewt, Position,); in step S102.2, the binding energy of wildtype Fab X VH and VL chains is computed with Rosetta score 12 function, termed as AGwt- In step S103, the wildtype residue on the current mutable position identified in step S101 are replaced (mutated) by the other amino acid types. Out of the 20 natural amino acid types, proline and cysteine are excluded from mutation. All the other 18 types (alanine, arginine, asparagine, aspartic acid, glutamic acid, glutamine, glycine, histidine, isoleucine, leucine, lysine, methionine, phenylalanine, serine, threonine, tryptophan, tyrosine, valine) except the wildtype itself are mutated on each mutable position one by one.

In step SI04, for each mutated residue type at each mutable position, the top 100 lowest-energy (in terms of Rosetta scoring function) rotamer states are generated using Rosetta. The other high energy rotamer states are discarded.

In step SI05, for each rotamer state of mutant residue generated in SI04, the IOTAScore is computed in the same way of step SI02, termed as (IOTAScore$_{mu}$tant, Position, Type$_k$, Rotamer,).

In step SI06, the AIOTAScore for the current combination of rotamer state, mutant residue type, and mutable position is computed by subtracting (IOTAScorewt, Position,) with (IOTAScore$_{mu}$tant, Position, Type$_k$, Rotamer,), which is termed as (AIOTAScore, Position,, Type$_k$, Rotamer,). Steps SI05 and SI06 were repeated to compute all of the AIOTAS cores for each rotamer states for the current mutant residue type and mutable position.

In step SI07, the optimal rotamer state of the current mutant residue type and mutable position is determined with the lowest AIOTAScore value, as shown in step S 107.1. The binding energy o f the mutant with the optimal rotamer state is computed in step SI07.2 in the same way as step S102.2, termed as ($AG_{mu}$tant, Position,-, Type/). In step S107.3, the change of binding energies ΔΔG between mutant and wild-type is calculated by subtraction of AGwt with $AG_{mu}$tant. After the optimal rotamer state is prioritised, steps SI03 to SI07 were repeated for the next mutant amino acid type at the current mutable position.

In step SI08, for the current mutable position, only the candidate mutants satisfying the criteria of both AIOTAS core<0 and ΔΔG<0 are kept for later ranking The rest are discarded. Steps SI02 to SI08 were repeated to go through all the mutable positions and generate all candidate mutants satisfying the same criteria.

In step SI09, all the candidate mutant structures were outputed for later visualisation analysis. The final list of candidate mutants were sorted and ranked by the lowest AIOTAS cores.

The running command and parameters used were as below:

For light chain mutations prediction, the command was:

"python multiRotamersFablnterfacelOTAScan.py ~pdb FabX.pdb –onlychains L-region all-useIOTA-IOTAtype 167 –output mutant"

For heavy chain mutations prediction, the command was:

"python multiRotamersFablnterfacelOTAScan.py ~pdb FabX.pdb –onlychains H-region all-useIOTA-IOTAtype 167 –output mutant"

Extra Rosetta relevant parameters were initialized by adding the following code to the "multiRotamersFablnterfacelOTAScan.py":

"init(extra_options="-ex1 -ex2 -score: weights score12 -no_his_his_pairE -constant_seed-edensity: mapreso 3.0 -correct-mute all"

DNA Manipulations and General Methods

*E. coli* strain INVaF (Invitrogen) was used for transformation and routine culture growth. DNA restriction and modification enzymes were obtained from Roche Diagnostics Ltd. and New England Bio labs. Plasmid preparations were performed using Maxi Plasmid™ purification kits (Qiagen, catalogue No. 12165). DNA sequencing reactions were performed using ABI Prism Big Dye™ terminator sequencing kit (catalogue No. 4304149) and run on an ABI 3100 automated sequencer (Applied Biosystems). Data was analysed using the program Auto Assembler (Applied Biosystems). Oligonucleotides were obtained from Invitrogen. The concentration of IgG was determined by IgG assembly ELISA.

Thermostability Improvement of Fab X Through Affinity Maturation of the Heavy-Light Chain Interface The wild type Fab fragment of Fab X and mutant variants were prepared as follows: oligonucleotide primer sequences were designed and constructed in order to introduce single point mutations in both the heavy and light chain variable regions as per residues and positions determined in the above short list. Each mutated light chain was separately sub-cloned into the UCB Celltech human light chain expression vector pKHIO.1, which contained DNA encoding the human C-kappa constant region (Km3 allotype). Each mutated heavy chain variable region sequence was separately sub-cloned into the UCB Celltech expression vector pVhglFab6His which contained DNA encoding human heavy chain gamma-1 constant region, CHI. Heavy and light chain encoding plasmids were co-transfected into HEK293 cells using the 293fectin™ procedure according to the manufacturer's instructions (InVitrogen. Catalogue No. 12347-019). IgG1 Fab antibody levels secreted into the culture supematants after 10 to 12 days culture were assessed by ELISA and binding kinetics assessed by surface plasmon resonance (see below).

Mutants showing improved thermostability were then prepared and tested in combination as double, or triple mutations as above.

Surface Plasmon Resonance (SPR)

All SPR experiments were carried out on a BIAcore T200 (GE Healthcare). Affinipure $F(ab')_2$ Fragment goat anti-human IgG, $F(ab')_2$ fragment specific (Jackson ImmunoResearch) was immobilised on a CMS Sensor Chip via amine coupling chemistry to a capture level of ≈5000 response units (RUs). HBS-EP buffer (10 mM HEPES pH 7.4, 0.15 M NaCl, 3 mM EDTA, 0.05% Surfactant P20, GE Healthcare) was used as the running buffer with a flow rate of 10 μL/minn. A 10 μL injection of Fab X at 0.75 μg/mL was used for capture by the immobilised anti-human IgG-$F(ab')_2$. Antigen was titrated over the captured Fab X at various concentrations (50 nM to 6.25 nM) at a flow rate of 30 μL/min. The surface was regenerated by 2×10 μL injection of 50 mM HCl, followed by a 5 μL injection of 5 mM NaOH at a flowrate of 10 μL/Min. Background subtraction binding curves were analysed using the T200evaluation software (version 1.0) following standard procedures. Kinetic parameters were determined from the fitting algorithm.

Thermostability Assay

Thermo fluor assay was performed to assess the thermal stabilities of purified molecules. Purified proteins (0.1 mg/ml) were mixed with SYPRO® Orange dye (Invitrogen), and the mixture dispensed in quadruplicate into a 384 PCR optical well plate. Samples were analysed on a 7900HT Fast Real-Time PCR System (Agilent Technologies) over a temperature range from 20° C. to 99° C., with a ramp rate of 1.1° C./min. Fluorescence intensity changes per well were plotted against temperature and the inflection points of the resulting slopes were used to generate the $T_m$.

Results

Intersection of Iota Density Maps with Heavy and Light Chain Atoms of the Interface The automated method using a Rosetta scan produced a table of mutations ranked by IOTA score (Table 6).

Effects of Iota Designed Mutations on Fab X on Thermostability

Figure 15:
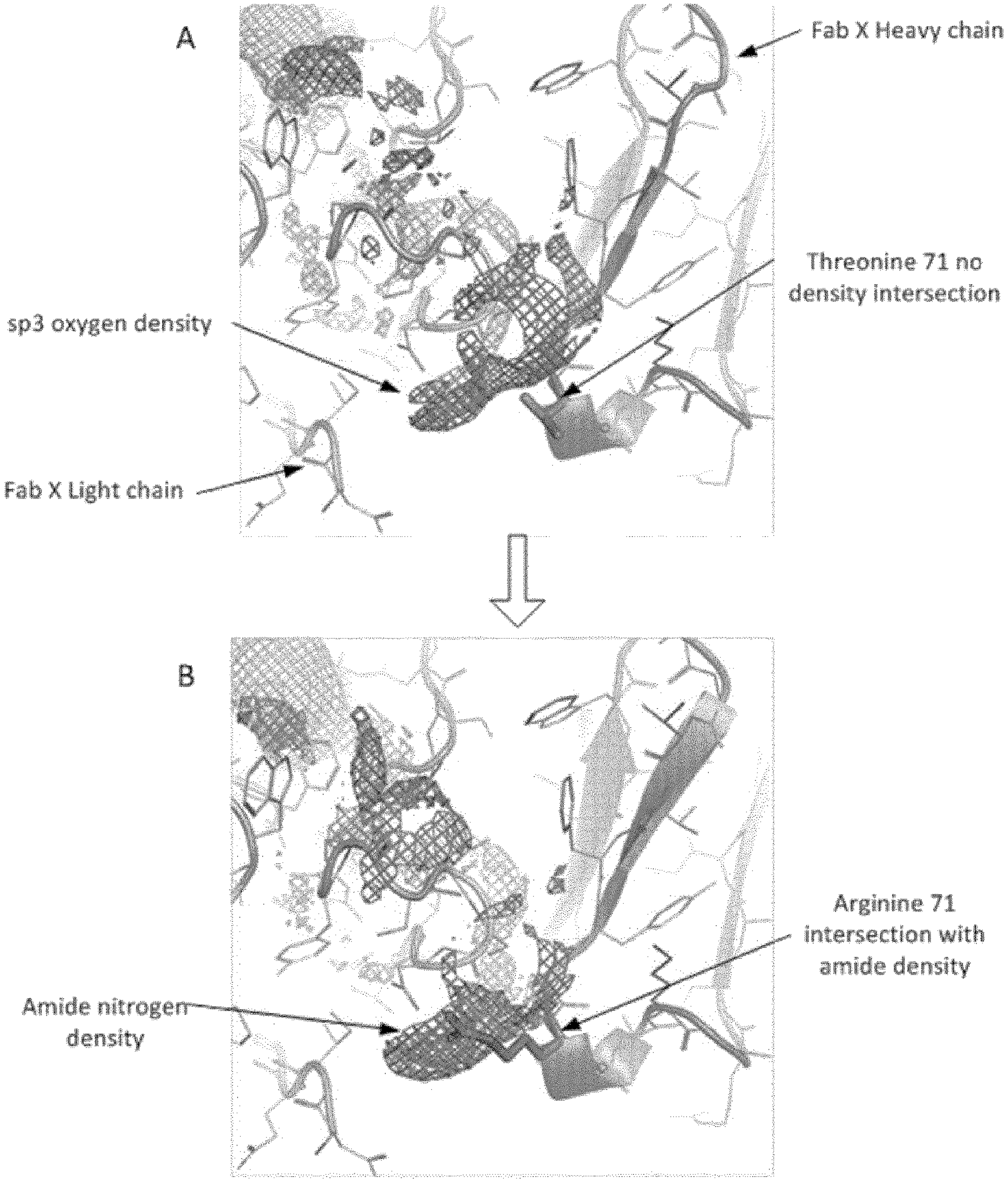
FIG. 15 is a computer generated visualisation depicting a heavy chain threonine 71 to arginine 71 mutation.
Figure 16:
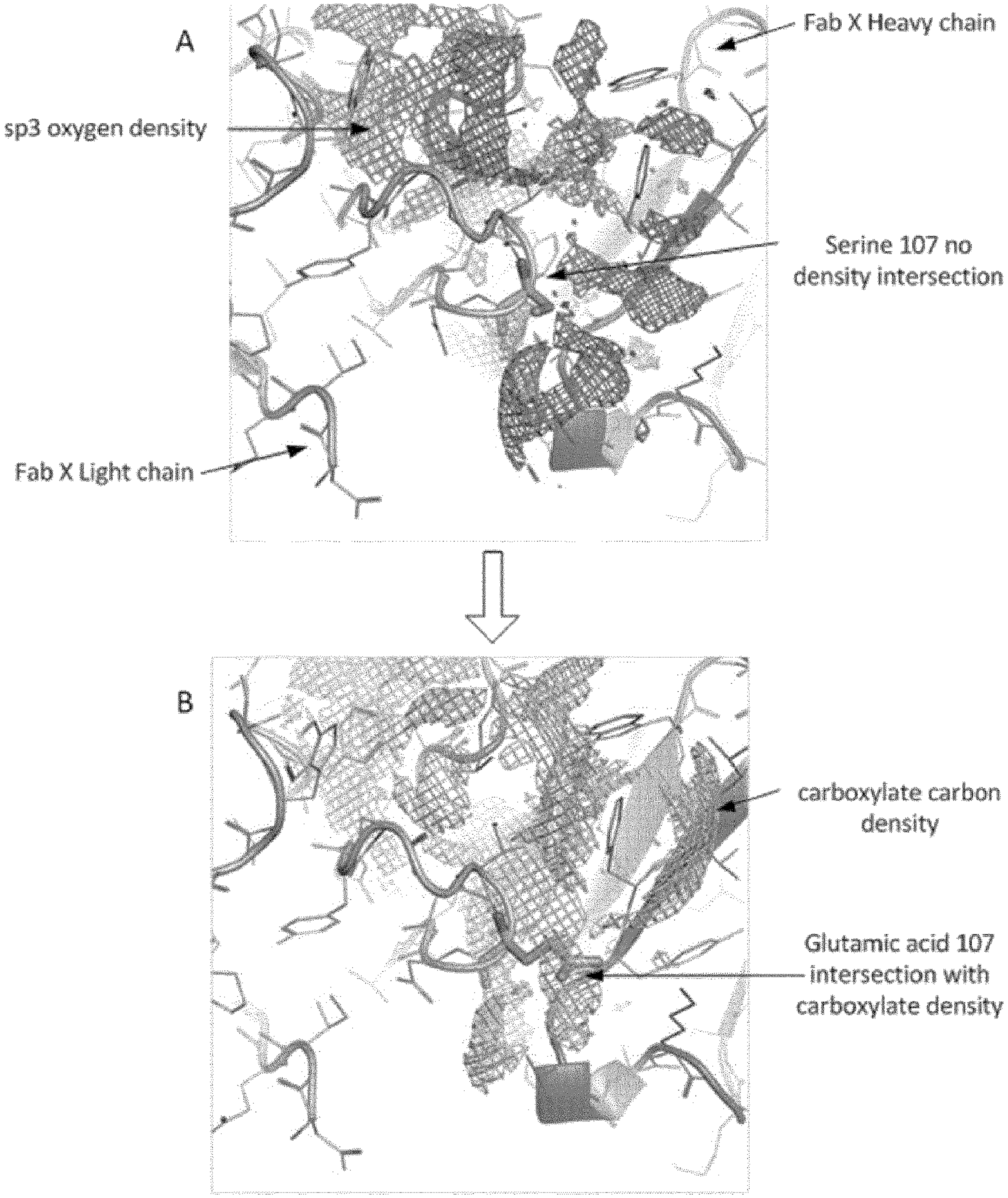
FIG. 16 is a computer generated visualisation depicting a light chain serine 107 to glutamic acid 107 mutation.
Figure 17:
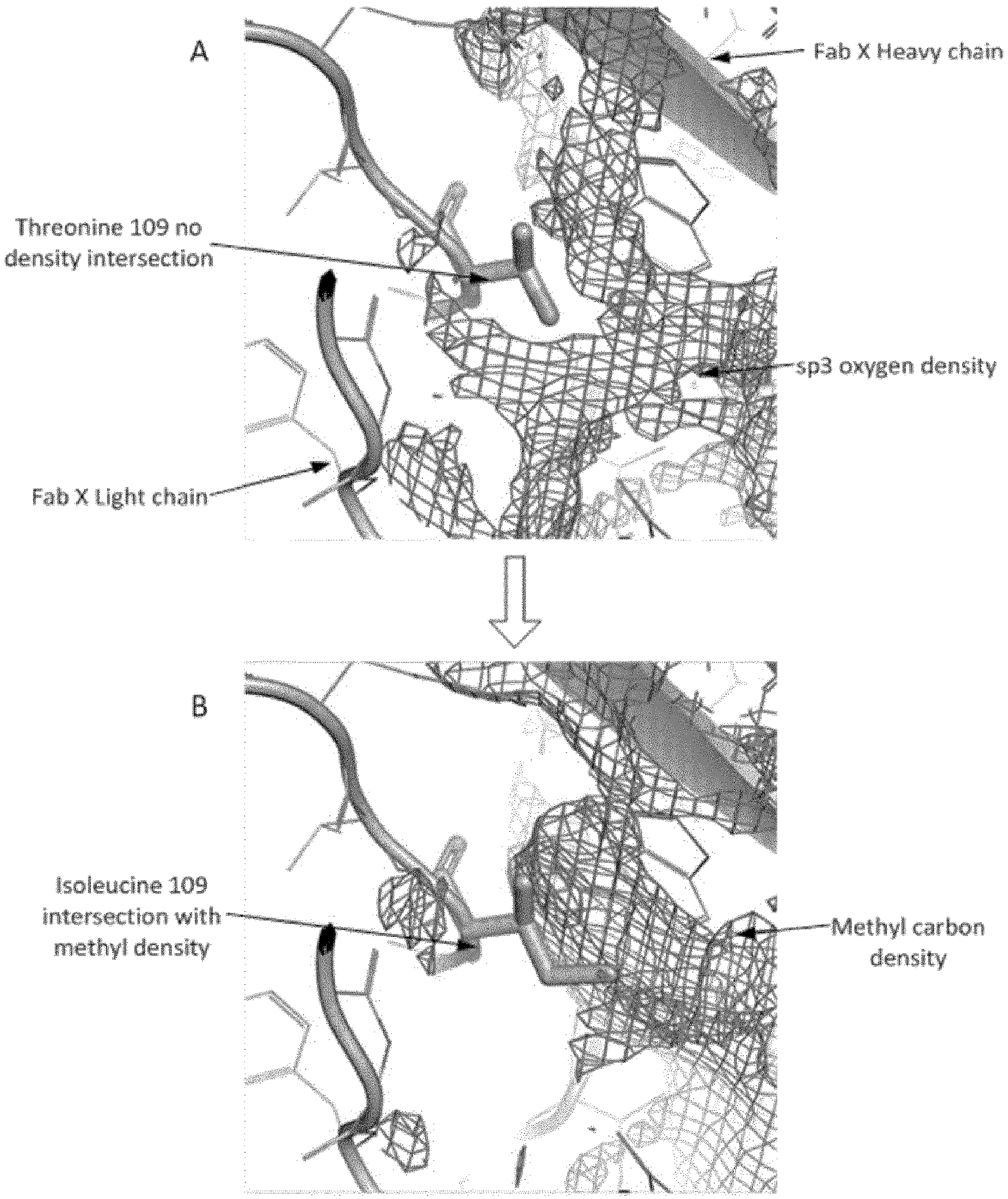
FIG. 17 is a computer generated visualisation depicting a light chain threonine 109 to isoleucine 109 mutation.

Six iota-designed single point mutations in Fab X, H-T71R, H-T71K , H-T71N, H-T71H, L-S 107E and L-T 1091, showed small improvements in thermostability ranging from 0.5° C. to 2.9° C. over wild-type (Table 7). FIGS. 15, 16 and 17 provide computer generated visualisations depicting the effects of these single point mutations. In particular, these Figures show that whilst H-T71, L-S 107 and L-T 109 have no density intersection, H-R71 intersects with the amide density, L-E107 intersects with the carboxylate density and L-I109 intersects with the methyl density. Combinations of these mutations in pairs resulted in a synergistic improvement in thermostability; with triple combinations producing further step improvements in thermostability (Table 8).

Figure 18:
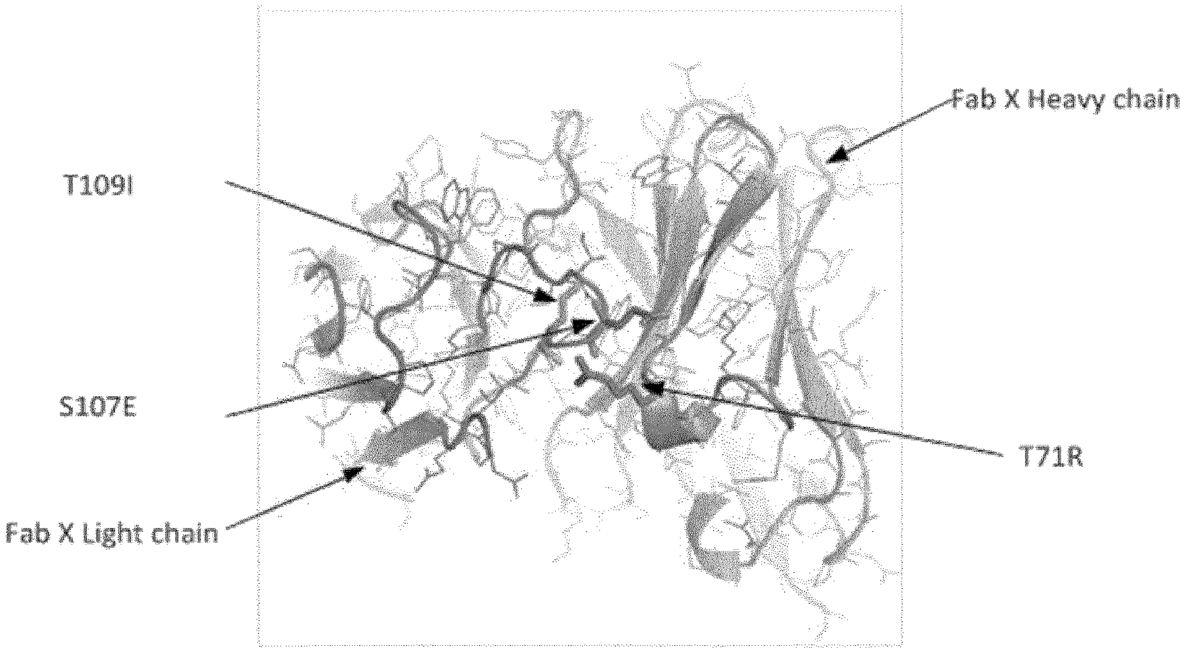
FIG. 18 is a computer generated visualisation depicting the combination of three mutations in Fab X resulting in a Tm of 81.2° C.

The combination of H-T71R, L-S107E and L-T 1091, mutations produced the largest improvement in thermostability (Table 8) to give a Tm of 81.2° C., some 5.8° C. better than the original Fab X. This combination of the three mutations is depicted in FIG. 18. An important finding was that there was no significant loss on the binding to its antigen.

TABLE 6

Proposed mutations generated by the Rosetta scan method and their ranking in order of IOTA score

| Rank (by IOTAScore) | Heavy chain | ΔΔG | ΔIOTA Score | Light chain | ΔΔG | ΔIOTA Score |
|---|---|---|---|---|---|---|
| 1 | T71R | −0.37 | −56.27 | T109H | −1.49 | −92.37 |
| 2 | V109R | −0.04 | −50.58 | T109K | −0.01 | −67.33 |
| 3 | V109K | −0.51 | −40.67 | T109I | −1.69 | −45.17 |
| 4 | T71H | −1.06 | −38.94 | I106L | −2.11 | −42.11 |
| 5 | T71K | −0.08 | −36.09 | T109L | −1.58 | −37.44 |
| 6 | T71W | −0.67 | −25.95 | I106H | −3.5 | −31.77 |
| 7 | T71Y | −0.67 | −25.64 | S107E | −0.62 | −18.71 |
| 8 | T71N | −0.03 | −24.89 | A53Y | −0.93 | −17.68 |
| 9 | D119W | −0.89 | −23.58 | A53F | −1.13 | −15.64 |
| 10 | T71Q | −0.38 | −23.28 | I106N | −0.47 | −13.57 |
| 11 | VI091 | −0.56 | −22.64 | | | |
| 12 | V109H | −0.4 | −21.73 | | | |

TABLE 7

Thermostability of mutations compared with wild-type thermostability of 75.7° C.

| Rank | Heavy chain | ΔΔG | ΔIOTA Score | Tm ° C. | Light chain | ΔΔG | ΔIOTA Score | Tm ° C. |
|---|---|---|---|---|---|---|---|---|
| 1 | T71R | −0.37 | −56.27 | 78.6 | T109H | −1.49 | −92.37 | 75.2 |
| 2 | V109R | −0.04 | −50.58 | 75.6 | T109K | −0.01 | −67.33 | ND |
| 3 | V109K | −0.51 | −40.67 | 75.6 | T109I | −1.69 | −45.17 | 79.2 |
| 4 | T71H | −1.06 | −38.94 | 76.6 | I106L | −2.11 | −42.11 | 74.5 |
| 5 | T71K | −0.08 | −36.09 | 78.6 | T109L | −1.58 | −37.44 | 77.6 |
| 6 | T71W | −0.67 | −25.95 | 75.6 | I106H | −3.5 | −31.77 | 72.2 |
| 7 | T71Y | −0.67 | −25.64 | 75.3 | S107E | −0.62 | −18.71 | 77.3 |
| 8 | T71N | −0.03 | −24.89 | 76.2 | A53Y | −0.93 | −17.68 | 68.8 |
| 9 | D119W | −0.89 | −23.58 | 73.7 | A53F | −1.13 | −15.64 | 67.2 |
| 10 | T71Q | −0.38 | −23.28 | 75.8 | I106N | −0.47 | −13.57 | 71.8 |
| 11 | V109I | −0.56 | −22.64 | ND | | | | |
| 12 | V109H | −0.4 | −21.73 | 75.1 | | | | |

ND = Not Determined

TABLE 8

Thermostability and affinity of combinations of mutations.

| Combination | Rosetta ddG (VH/VL) | Rosetta dE (Fv) | Tm (° C.) | Tm SD | KD (nM) |
|---|---|---|---|---|---|
| H-T71R + L-S107E + L-T109I | −3.72 | −1.73 | 81.2 | 0.3 | ND |
| H-T71R + L-T109I | −2.3 | −1.17 | 80.1 | 0 | 0.88 |
| H-T71R + L-S107E | −2.13 | −0.93 | 80.1 | 0 | 3.90 |
| H-T71K + L-S107E | −0.3 | 0.76 | 79.4 | 0.6 | 3.50 |
| H-T71K + L-S107E + L-T109L | −4.11 | −1.41 | 79.3 | 0.3 | ND |
| H-T71K + L-T109I | −1.96 | −0.98 | 79.1 | 0.3 | 1.39 |
| H-T71R + L-T109L | −2.77 | −0.95 | 78.0 | 0.6 | 0.96 |
| H-T71K + L-T109L | −2.2 | −0.7 | 77.7 | 0.1 | 1.59 |
| H-T71R | −0.37 | | 78.0 | 0.3 | 0.80 |
| H-T71K | −0.08 | | 77.9 | 0.3 | 1.27 |
| L-S107E | −0.62 | | 77.3 | 0.5 | 5.52 |
| L-T109I | −1.69 | | 77.9 | 0.3 | 1.47 |
| L-T109L | −1.58 | | 76.9 | 0.5 | 1.73 |
| WT | | | 75.4 | 0.2 | 1.35 |

ND = Not Determined

The invention claimed is:

1. A method for manufacturing a ligand having affinity for a binding site of a macromolecular target, the method comprising designing the ligand by:

a) identifying, by one or more processors of a computing system, a target list of atoms forming a surface of the binding site, wherein the atoms in the target list are referred to as target theta atoms;

b) classifying, by the one or more processors, the target theta atoms according to atom type, wherein the atom types of the target theta atoms are referred to as target theta atom types and are selected from a predetermined list of possible theta atom types;

c) extracting, by the one or more processors and from a structural database of biological macromolecules, information about non-bonding, intra-molecular or inter-molecular atom to atom contacts, wherein an atom type of a reference theta atom in a contacting pair of atoms is one of the predetermined list of possible theta atom types, and wherein the atom type of an opposing, reference iota atom of the pair, is one of a predetermined list of possible iota atom types, wherein the information comprises spatial data about the reference iota atom relative to the reference theta atom;

d) collecting, by the one or more processors and from the structural database, data comprising a theta contact set for a plurality of contacts involving further reference theta atoms of the atom type;

e) for each target theta atom identified in the target list, the one or more processors: superimposing, in or around the binding site, data relating to a given iota atom type, or a predetermined group of related iota atom types, from a corresponding theta contact set, the superimposition comprising using the spatial data in the theta contact set for contacts comprising the given iota atom type or one or more of the predetermined group of related iota atom types to determine theoretical locations representing where each iota atom type, or each of the one or more of the predetermined group of related iota atom types, would be located if the theta atom of the contact were located at the position of the corresponding theta atom in the target binding site;

f) combining or parsing, by the one or more processors, the data to predict one or more favored regions of the binding site where the given iota atom type, or the predetermined group of related iota atom types, has high theoretical propensity to be located, the high theoretical propensity being defined as where a density of the determined theoretical locations is above a threshold; and g) identifying a modification to a candidate ligand, in terms of alternate or additional atoms within the candidate ligand, that produces a greater intersection between the alternate or additional atoms and the favored regions for the respective iota atom types, leading to an improvement in affinity of the candidate ligand as modified to the binding site compared to the candidate ligand without modification, by notionally docking the un- modified candidate ligand into the binding site and comparing, by the one or more processors, the type and position of one or more of the atoms of the candidate ligand with the favored regions for the respective iota atom types;

wherein each non-bonding intra-molecular or inter-molecular contact in the structural database is defined as a contact between opposing residues of a protein fold or between opposing monomer units of a macromolecular fold or between two interacting macromolecular partners and is between a particular reference theta atom on one side of the fold or first interacting partner and a particular reference iota atom on an opposing side or second interacting partner, in an instance where the following condition is satisfied:

s-Rw<t, wherein s represents separation between two atoms of the contact, Rw represents a sum of van der Waals radii of the two atoms of the contact, and t represents a predetermined threshold distance; and wherein the classification by target theta atom type is unique such that there is no intersection between the data of any theta contact set for a given theta atom type and the data of any other theta contact set for any other theta atom type, apart from data representing contacts involving the given theta atom as the iota atom;

wherein the predetermined group of related iota atom types is one of a plurality of non-overlapping groups obtained by sorting the 167 non-hydrogen atoms present in the 20 natural amino acids of proteins into groups of similar chemical type; and manufacturing the candidate ligand as modified, wherein the candidate ligand as modified is an antibody.

2. The method according to claim 1, wherein for each non- bonding intra-molecular contact extracted from the structural database, the following condition is also satisfied:

the reference theta atom and the reference iota atom of the contact are on different residues separated by at least four residues along a linear polypeptide or are on separate polypeptide chains.

3. The method according to claim 1, wherein the classification by target theta atom type comprises identifying each target theta atom as being one and only one of:

the 167 non-hydrogen atoms present in the 20 natural amino acids of proteins;

the 82 non-hydrogen atoms present in the 4 nucleotides of the deoxyribonucleic acid polymer (DNA);

the 42 non-hydrogen atoms present in the methylated DNA nucleotides, cytidine phosphate and adenosine phosphate;

the 85 non-hydrogen atoms present in the 4 nucleotide phosphates of the ribonucleic acid polymer (RNA);

the 89 non-hydrogen atoms present in 2-0'-methylated ribose nucleotide phosphates of RNA;

the over 400 non-hydrogen atoms present in the commonest post-transcription base modified RNA.

4. The method according to claim 1, wherein the information extracted is collected in a secondary database comprising one and only one theta contact set for each of the theta atom types.

5. The method according to claim 4, wherein each of the theta contact sets in the secondary database is sub-divided into a plurality of non-overlapping iota atom types or non-overlapping groups of related iota atom types.

6. The method according to claim 1, wherein the iota atom types are sorted into the plurality of non-overlapping groups according to one or more of the following factors: elemental nature of the iota atom types or hybridisation state of the iota atom types.

7. The method according to claim 1, wherein the iota atom types are sorted into a plurality of non-overlapping groups comprising the following: C $sp^3$, C $sp^2$ (aromatic), C $sp^2$ (non-aromatic), N $sp^3$, N $sp^2$, O $sp^3$, O $sp^2$, and S.

8. The method according to claim 1, wherein the spatial data defines a position of each reference iota atom specified in the theta contact set by geometrical reference to a position of the reference theta atom and to positions of third and fourth atoms, and wherein the third atom is covalently bonded to the reference theta atom, and wherein the fourth atom is covalently bonded to the third atom.

9. The method according to claim 8, wherein for each reference iota atom specified in the theta contact set, the spatial data defines a position of fifth and sixth atoms by geometrical reference to the position of the reference theta atom and to the positions of the third and fourth atoms, wherein the fifth atom is covalently bonded to the reference iota atom, and wherein the sixth atom is covalently bonded to either the fifth atom or the reference iota atom.

10. The method according to claim 9, wherein the superimposition comprises parsing the theta contact set to extract spatial data for contacts comprising the given iota atom type or one or more of the predetermined group of related iota atom types, and plotting this spatial data to determine theoretical locations representing where each iota atom type, or each of the one or more of the predetermined group of related iota atom types, would be located if: i) the reference theta atom of the contact were located at the position of the corresponding target theta atom in the target binding site; and ii) the third and fourth atoms of the contact were located at the positions of the third and fourth atoms of the corresponding target theta atom in the target binding site.

11. The method according to claim 10, wherein the information about non-bonding, intra-molecular or inter-molecular atom to atom contacts further comprises contextual data about the reference iota atom relative to the reference theta atom, and wherein the spatial data is parsed against said contextual data before the plotting.

12. The method according to claim 10, wherein a region in which a density of the theoretical locations for the given iota atom type, or for the one or more of the predetermined group of related iota atom types, is above a predetermined threshold is identified as one of the favored regions.

13. The method according to claim 10, wherein the theoretical locations for the given iota atom type, or for one or more of the predetermined group of related iota atom types, are determined for a plurality of target theta atoms on the target list and a region in which a density of cumulative theoretical locations is above the predetermined threshold is identified as one of the favored regions.

14. The method according to claim 10, further comprising determining whether a theoretical location of an individual reference iota atom intersects with a location of an atom of the target macromolecule closer than Rw-0.2 angstroms, and responsively excluding the reference iota atom from subsequent analysis.

15. The method according to claim 9, wherein the third and fourth atoms are chosen uniquely for each specified theta atom type.

16. The method according to claim 9, wherein for each of the favored regions, vectors are derived to describe the position of the fifth atom relative to its respective reference iota atom and analysis is carried out on the vectors in order to identify a favored bond vector representing a prediction of the covalent attachment of a theoretical consensus reference iota atom in the region, the favored bond vector being used to refine a design of the candidate ligand or modification of the candidate ligand.

17. The method according to claim 1, wherein the information about non-bonding, intra-molecular or inter-molecular atom to atom contacts further comprises contextual data about the reference iota atom relative to the reference theta atom, and wherein the contextual data contains contextual information concerning a local environment of each contact pair in the theta contact set, including one or more of: secondary structure, amino acid types or other monomer types comprising the contact pair, adjacent monomer units or local geometry thereof in a polymer chain either side of the contact, adjacent amino acids in a polypeptide chain on either side of the contact, local geometry of the adjacent monomer units or amino acids, temperature factor of the reference theta atom, temperature factor of the reference iota atom, accessible surface area of the reference theta atom, accessible surface area of the reference iota atom, a number of different reference iota atom contacts for the particular reference theta atom, or a number of other reference theta atoms on the same monomer unit as the reference theta atom.

18. The method according to claim 1, wherein comparing the type and position of one or more of the atoms of the candidate ligand with the favored regions for the respective iota atom types comprises identifying a modification of the candidate ligand that increases a degree of overlap between one or more atoms of the candidate ligand and a predicted favored region or regions for an iota atom type or predetermined group of related iota atom types in the binding site.

19. The method according to claim 1, wherein a plurality of modifications to the candidate ligand are identified, and the method further comprises selecting a subset of the identified modifications based on one or both of: 1) an extent to which the intersection between the alternate or additional candidate ligand atoms and the respective iota atom type favored regions is greater compared to the candidate ligand without modification; or 2) an extent to which one or more factors contributing to a total energy of a complex formed by binding of the candidate ligand as modified to the binding site are reduced compared to a case where the candidate ligand without modification is bound.

* * * * *